United States Patent [19]

Conway et al.

[11] Patent Number: 5,360,402
[45] Date of Patent: Nov. 1, 1994

[54] HAND-ACTUATED RETENTION CATHETER

[75] Inventors: Anthony J. Conway; Philip J. Conway, both of Chatfield; Richard D. Fryar, Jr., Rochester, all of Minn.

[73] Assignee: Rochester Medical Corporation, Stewartville, Minn.

[21] Appl. No.: 827,936

[22] Filed: Jan. 29, 1992

Related U.S. Application Data

[63] Continuation-in-part of Ser. No. 809,281, Dec. 13, 1991, which is a continuation-in-part of Ser. No. 489,462, Mar. 6, 1990, abandoned, which is a continuation-in-part of Ser. No. 487,422, Mar. 1, 1990, Pat. No. 5,098,379, which is a continuation-in-part of Ser. No. 462,832, Jan. 10, 1990, Pat. No. 5,137,671.

[51] Int. Cl.$^5$ .......................................... A61M 29/00
[52] U.S. Cl. .......................................... 604/97; 604/96
[58] Field of Search ............................ 604/96–103, 604/174, 178, 264, 280; 606/192–196

[56] References Cited

U.S. PATENT DOCUMENTS

| | | | |
|---|---|---|---|
| 1,235,142 | 7/1917 | Ichilian | 604/97 |
| 1,643,289 | 9/1927 | Peglay | 604/97 |
| 3,044,468 | 7/1962 | Birtwell | 604/97 |
| 3,053,257 | 9/1962 | Birtwell | 604/97 |
| 3,169,527 | 2/1965 | Sheridan . | |
| 3,544,668 | 12/1970 | Dereniuk . | |
| 3,556,294 | 1/1971 | Walck, III et al. | 206/63.2 |
| 3,566,874 | 3/1971 | Shepherd et al. . | |
| 3,593,713 | 7/1971 | Bogoff et al. | 128/426 |
| 3,598,127 | 8/1971 | Wepsic . | |
| 3,683,928 | 8/1972 | Kuntz . | |
| 3,699,956 | 10/1972 | Kitrilakis et al. | 128/348 |
| 3,708,324 | 1/1973 | Stebleton | 117/47 R |
| 3,854,483 | 12/1974 | Powers . | |
| 3,875,937 | 4/1975 | Schmitt et al. . | |
| 3,894,540 | 7/1975 | Bonner, Jr. . | |
| 3,924,634 | 12/1975 | Taylor et al. . | |
| 4,062,363 | 12/1977 | Bonner, Jr. . | |
| 4,269,310 | 5/1981 | Uson | 206/210 |
| 4,318,947 | 3/1982 | Joung | 428/36 |
| 4,378,796 | 4/1983 | Millaud | 128/207.15 |
| 4,381,008 | 4/1983 | Thomas et al. | 604/265 |
| 4,381,380 | 4/1983 | LeVeen et al. | 525/452 |
| 4,479,795 | 10/1984 | Mustacich et al. | 604/53 |
| 4,515,593 | 5/1985 | Norton | 604/265 |
| 4,539,234 | 9/1985 | Sakamoto et al. | 427/393 |
| 4,563,184 | 1/1986 | Korol | 604/368 |
| 4,581,028 | 4/1986 | Fox, Jr. et al. | 623/2 |
| 4,582,762 | 4/1986 | Onohara et al. | 428/447 |
| 4,592,920 | 6/1986 | Murtfeldt | 427/2 |
| 4,603,152 | 7/1986 | Laurin et al. | 604/265 |

(List continued on next page.)

FOREIGN PATENT DOCUMENTS

| | | |
|---|---|---|
| 763930 | 7/1967 | Canada . |
| 0055023 | 6/1982 | European Pat. Off. . |
| 0218157 | 12/1984 | Japan . |
| 0228856 | 12/1984 | Japan . |
| 2150938 | 7/1985 | United Kingdom . |
| 278468 | 10/1970 | U.S.S.R. . |
| 84/01102 | 3/1984 | WIPO . |
| 89/09626 | 10/1989 | WIPO . |

OTHER PUBLICATIONS

R. Bayston, *Devel. Medicine and Child Neurol.* Suppl. (37): 50–54 (1976).

(List continued on next page.)

*Primary Examiner*—John D. Yasko
*Assistant Examiner*—Adam Cermak
*Attorney, Agent, or Firm*—Merchant, Gould, Smith, Edell, Welter & Schmidt

[57] ABSTRACT

A hand-actuated retention catheter 5 is disclosed. The retention catheter includes a tube 12, an overcoat layer 14 encircling the tube 12 and a cavity 16 interposed between the tube 12 and the overcoat layer 14. The cavity 16 encircles the tube and includes a bulbous balloon portion 24 and an enlarged fluid reservoir portion 22 interconnected and separated by a catheter sleeve portion 26 which has a narrowed outside diameter. The expandable balloon portion 24 can be expanded by compressing the fluid reservoir portion 22. Methods of making the hand-actuated retention catheter and methods of using the same are also disclosed.

20 Claims, 15 Drawing Sheets

U.S. PATENT DOCUMENTS

| | | | |
|---|---|---|---|
| 4,622,033 | 11/1986 | Taniguchi | 604/172 |
| 4,623,329 | 11/1986 | Drobish et al. | 604/29 |
| 4,634,433 | 1/1987 | Osborne | 604/171 |
| 4,652,259 | 3/1987 | O'Neil | 604/54 |
| 4,664,657 | 5/1987 | Williamitis et al. | 604/265 |
| 4,677,143 | 6/1987 | Laurin et al. | 523/122 |
| 4,686,124 | 8/1987 | Onohara et al. | 428/35 |
| 4,687,470 | 8/1987 | Okada | 604/171 |
| 4,710,181 | 12/1987 | Fugua | 604/280 |
| 4,747,845 | 5/1988 | Korol | 604/368 |
| 4,769,013 | 9/1988 | Lorenz et al. | 604/265 |
| 4,772,473 | 9/1988 | Patel et al. | 424/457 |
| 4,813,935 | 3/1989 | Haber et al. | 604/99 |
| 4,820,292 | 4/1989 | Korol et al. | 435/32 |
| 4,838,876 | 6/1989 | Wong et al. | 604/265 |
| 4,863,424 | 9/1989 | Blake, III et al. | 604/54 |
| 4,863,444 | 9/1989 | Blomer | 604/304 |
| 4,902,503 | 2/1990 | Umemura et al. | 424/83 |
| 4,917,686 | 4/1990 | Bayston et al. | 604/265 |
| 4,923,450 | 5/1990 | Maeda et al. | 604/265 |
| 4,925,668 | 5/1990 | Khan et al. | 424/422 |
| 4,935,260 | 6/1990 | Shlenker | 427/2 |
| 4,950,256 | 8/1990 | Luther et al. | 604/265 |
| 4,968,507 | 11/1990 | Zentner et al. | 424/465 |
| 4,976,703 | 12/1990 | Franetzki et al. | 604/247 |
| 4,981,471 | 1/1991 | Quinn et al. | 604/97 |
| 5,013,306 | 5/1991 | Solomon et al. | 604/265 |
| 5,013,717 | 5/1991 | Solomon et al. | 604/265 |
| 5,019,096 | 5/1991 | Fox, Jr. et al. | 623/1 |
| 5,019,378 | 5/1991 | Allen | 424/78 |
| 5,019,601 | 5/1991 | Allen | 523/122 |

OTHER PUBLICATIONS

R. Bayston, *J. Pediatric Surgery* 12: 55–61 (1977).

J. C. Brocklehurst et al., *Brit. J. Urology* 50(2): 102–105 (1978).

H. K. Butler et al., *J. Urology* 100: 560–566 (1968).

A. M. Johansen and B. Sorensen, *Scand. J. Plast. Reconstr. Surg.* 6(1): 47–50 (1972).

S. M. Lazarus et al., *J. Biomed. Materials Res.* 5: 129–138 (1971).

K. Miura et al., "The Nitrofurans," in *Progress in Medicine Chemistry*; vol. 5 (G. P. Ellis & G. B. West, Eds.); 1967; New York, N.Y.; Plenum; pp. 320–381.

T. Monson et al., *J. Urology* 111: 220–222 (1974).

H. Mooro et al., *J. Egypt. Med. Assoc.* (*Egypt*) 49(8): 550–553 (1966).

J. L. Nosher et al., *Cardiovasc. Interventional Radiol.* 13: 102–106 (1990).

M. Rehula, *Cesk. Farm.* (Czechoslovakia) 39/10: 436–437 (1990).

*Cesk. Farm.* (Czechoslovakia) 39/8: 349–352 (1990).

D. N. Rushton et al., *J. Neurol., Neurosurg., Psych.* 52: 223–229 (1989).

I. Sakamoto et al., *J. Biomed. Materials Res.* 19: 1031–1041 (1985).

Z. Shah et al., *Plastic and Reconstr. Surg.* 69:809–814 (1982).

R. Van Noort, *J. Biomed. Materials Res.* 13: 623–630 (1979).

The Bard Hospital Division Brochure (copyright on a date unknown prior to Nov. 9, 1989 by C. R. Bard, Inc., Murray Hill, N.J. 07974).

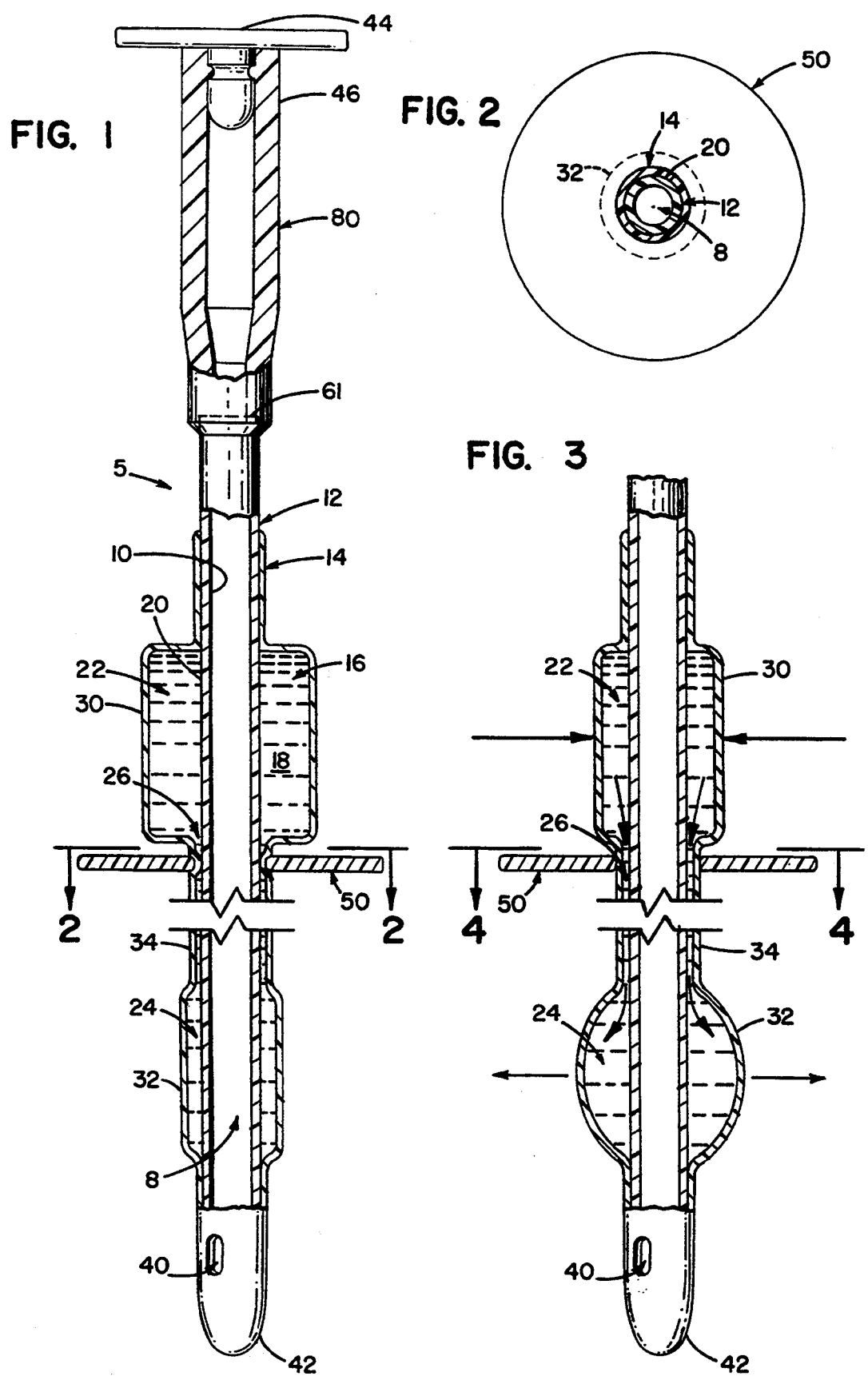

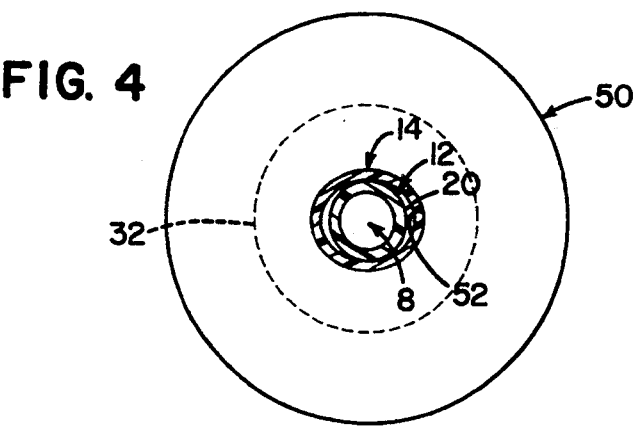
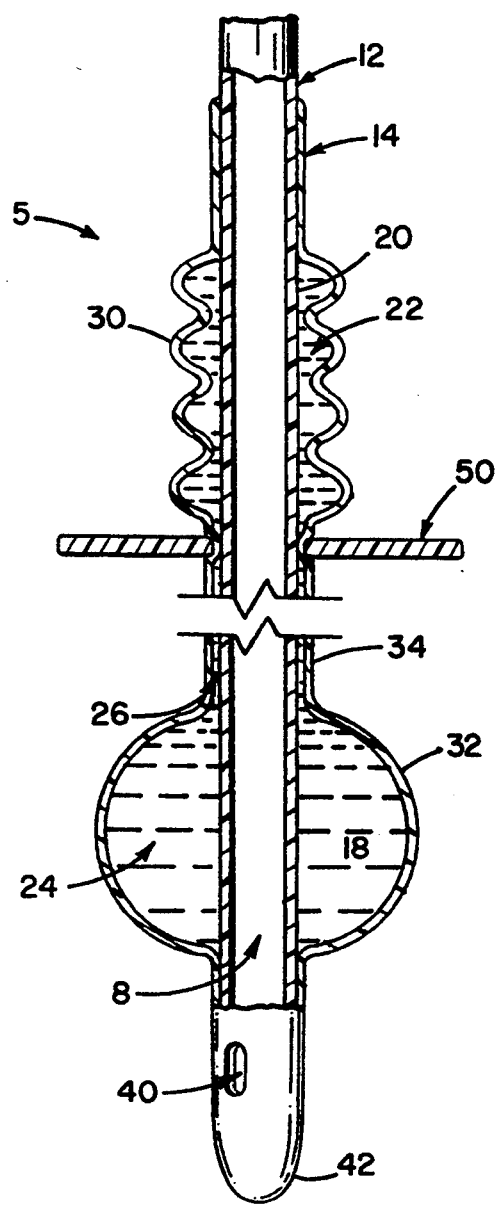

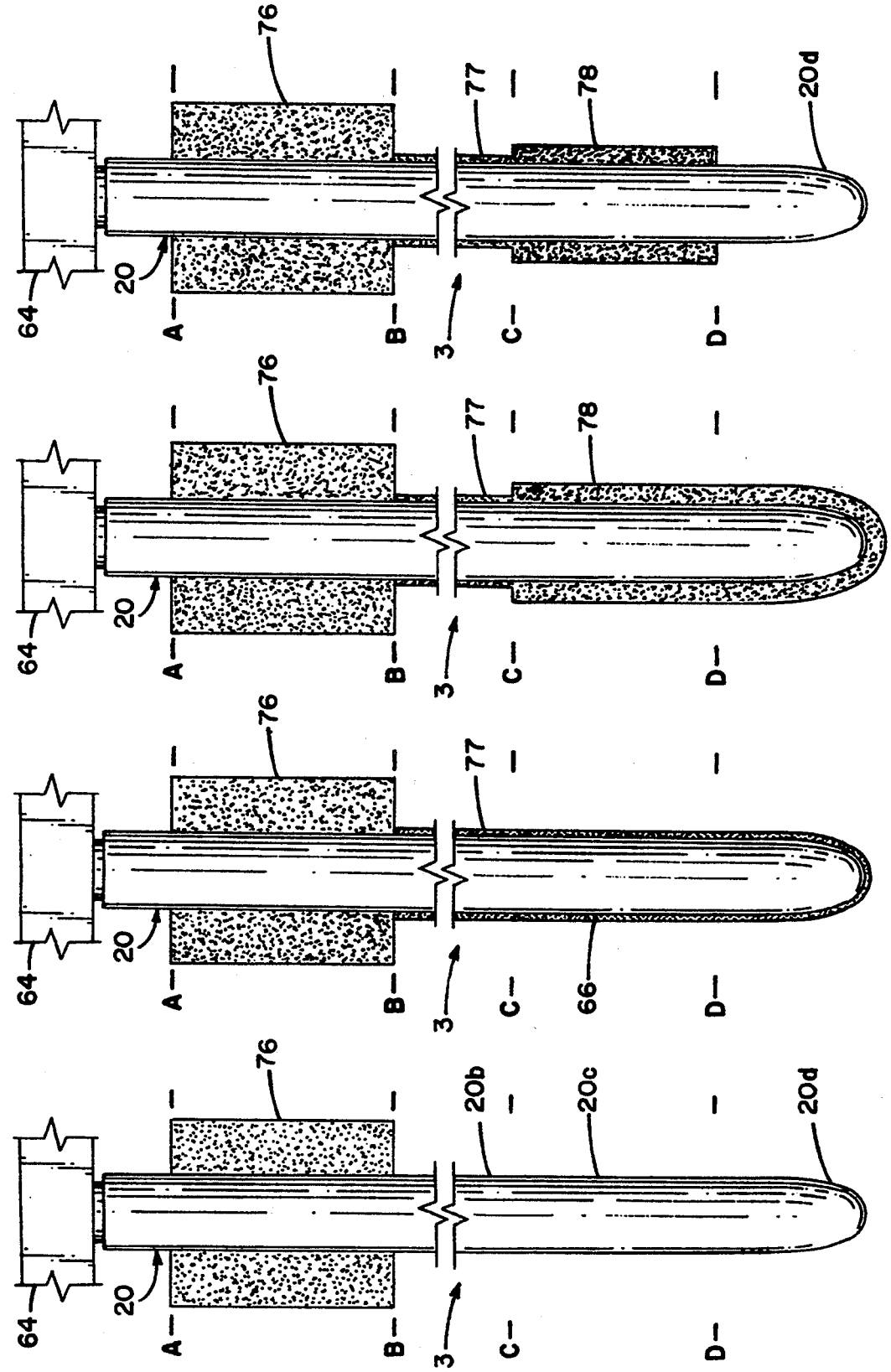

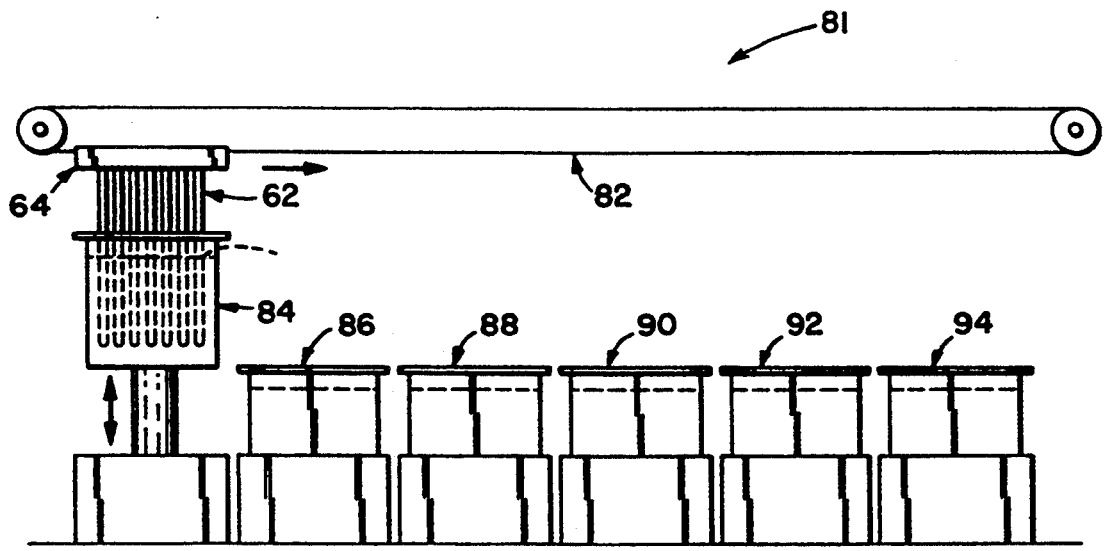
FIG. 19
FIG. 20A
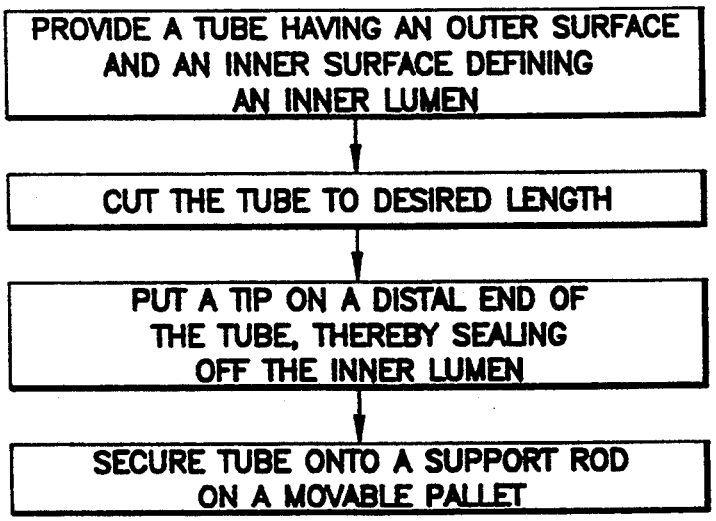

FIG. 20C
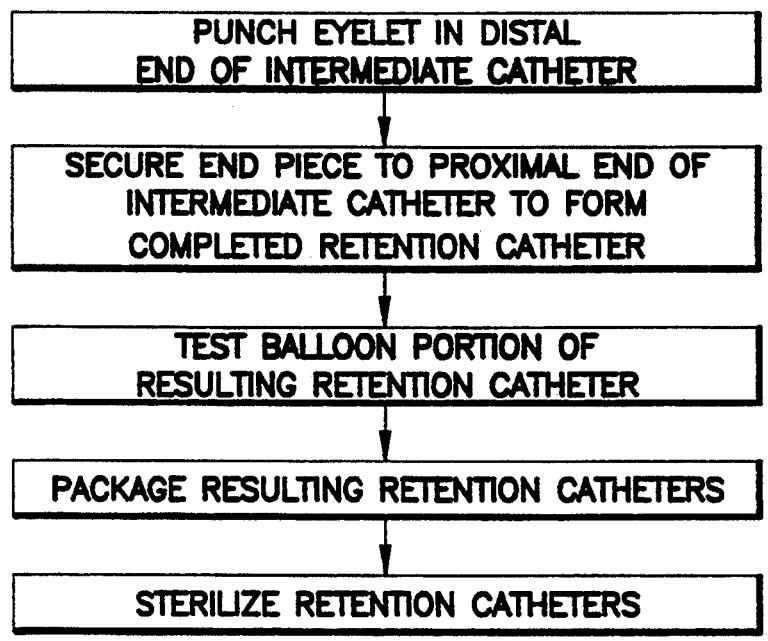
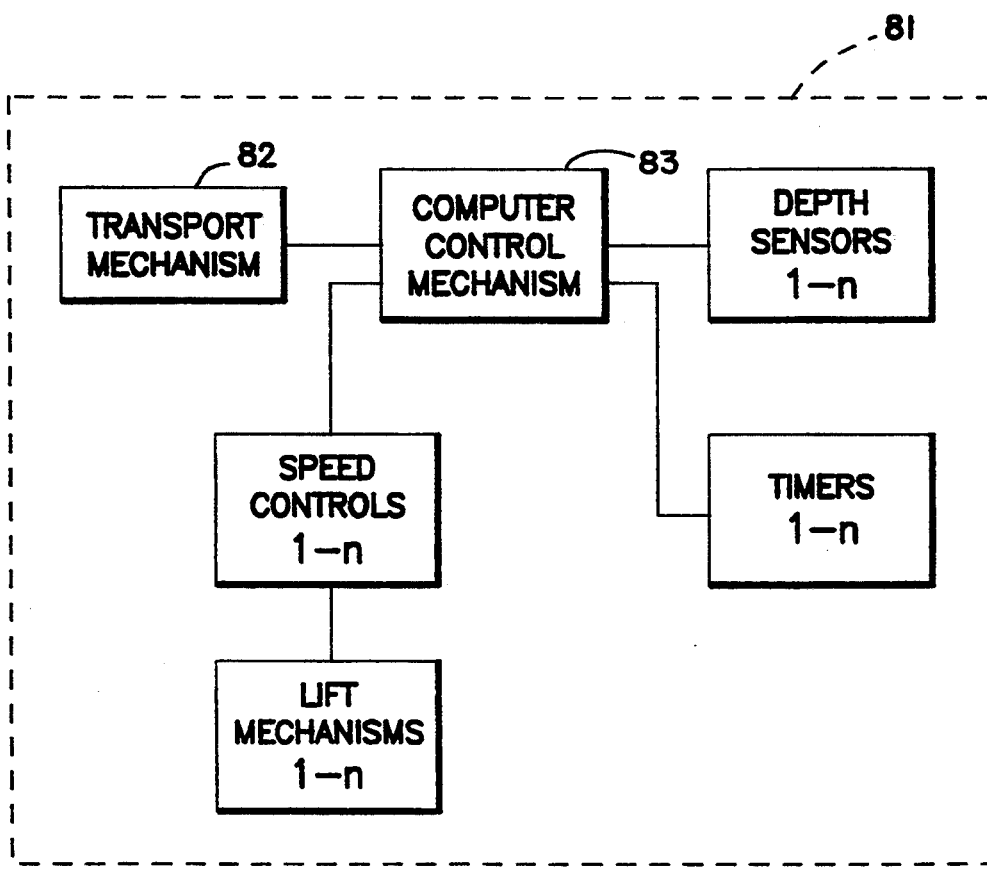
FIG. 21

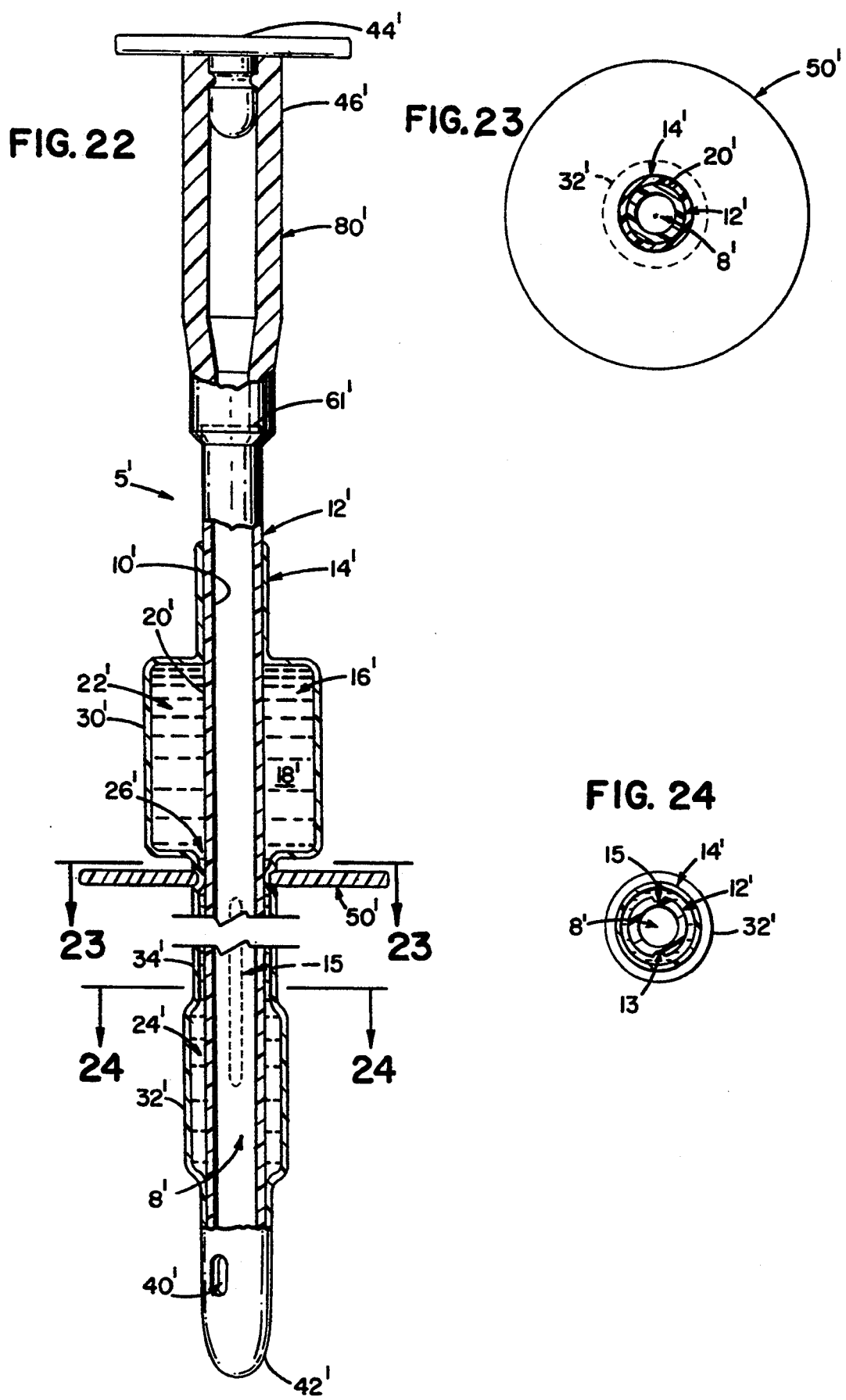

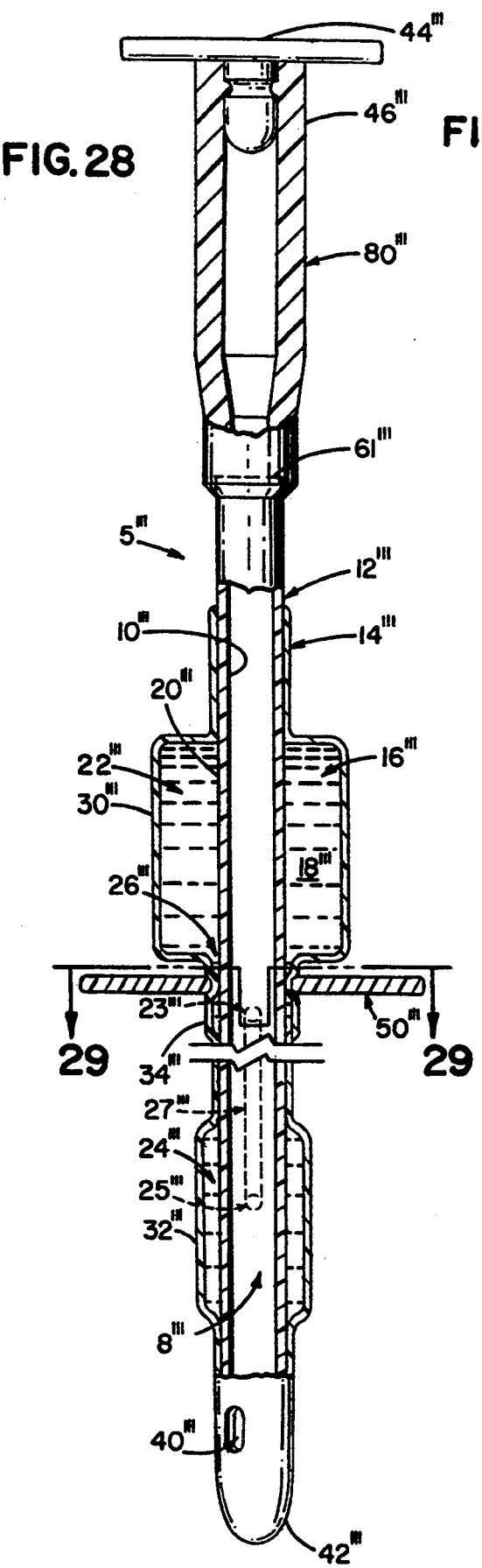
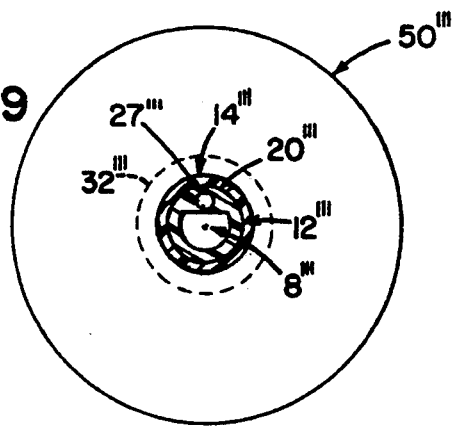
FIG. 28
FIG. 29

HAND-ACTUATED RETENTION CATHETER

CROSS-REFERENCE TO OTHER APPLICATIONS

The present application is a continuation-in-part application of co-pending U.S. patent application Ser. No. 07/809,281, filed Dec. 13, 1991, which is a continuation-in-part of co-pending U.S. patent application Ser. No. 07/489,462, filed Mar. 6, 1990, now abandoned, which is a continuation-in-part application of co-pending U.S. patent application Ser. No. 07/487,422, filed Mar. 1, 1990, now U.S. Pat. No. 5,098,379, which is a continuation-in-part application of co-pending U.S. patent application Ser. No. 07/462,832, filed Jan. 10, 1990, now U.S. Pat. No. 5,137,671, the disclosures of which are each incorporated herein by reference.

FIELD OF THE INVENTION

The present invention relates to balloon catheters which are either implantable or insertable into a human body, particularly hand-actuated balloon catheters. These devices have expandable retention balloons which can be expanded once the device is positioned within the body, thereby providing a mechanism for preventing the removal of the catheter once it is so positioned. The present invention also relates to methods for making the same, products made by these methods, and methods of using the hand-actuated balloon catheter.

BACKGROUND OF THE INVENTION

Catheters are tube like devices which are inserted into a portion of a person's body in order to transport fluids, such as liquids, gases, and sometimes semisolids, in or out of that particular portion of the body. For instances, urinary catheters are used to transport urine collected in the bladder out of the body via the urinary tract. Other types of catheters such as gastronomy devices, transport fluids into and out of various segments of the gastrointestinal system, primarily the stomach.

In order to provide a means of retaining the catheter within the body, inflatable bag catheters were introduced many years ago. Subsequently, Foley (U.S. Pat. No. 3,409,016) taught an elongated catheter having a secondary lumen for inflating a retention balloon at a distal end of the catheter once the distal end is positioned within the body. Such catheters are now generally referred to as "Foley" catheters out of respect for the contribution made by Dr. Foley.

Improvements on Dr. Foley's contribution to the catheter art continue to find their way into the market place today. In spite of the many practical uses for these devices today, they do have limitations, a few of which are discussed below. First, they are difficult for untrained individuals to use, especially relatively untrained nursing home attendants and/or patient's who may wish to care for their own needs. Second, because the fluid to expand the balloon is delivered from an external source, it is possible to burst the balloon by injecting too much fluid. It will be appreciated that this creates a safety concern. Third, it is possible that the secondary lumen which communicates with the cavity of the expandable balloon may become clogged during use of the catheter, thereby creating a problem when it becomes time to deflate the expandable balloon and remove the catheter. Fourth, the outer surface of the catheter leading to the balloon can irritate internal surfaces of the body with which it comes into contact, thereby creating inflamed areas which can be painful to the patient and may be more susceptible to bacterial infection. Fifth, the conduit portion of the catheter immediately adjacent to the expandable balloon does not fully engage or conform to the internal surfaces of the body approximate the expandable balloon. In the case of a urinary catheter, this often enables urinary fluids from the bladder to pass through the sphincter at the proximal end of the urinary passageway, thereby allowing urinary fluids to leak out of the bladder into the urinary passageway, thereby creating a risk of infection for the catheterized patient. Sixth, the cost of manufacturing traditional Foley catheters has been influenced by the need to use a significant amount of hand labor to make the devices. It will be appreciated that efforts to reduce the amount of hand labor in the manufacture of such devices may reduce the cost of such devices so that they are more competitive in the market place.

It will be appreciated, therefore, that there is a need for a retention catheter, as well as methods for making and using the same, which will address these and other problems associated with prior art devices and methods. The present invention provides advantages over the prior art catheters, over the prior art methods for manufacturing and using the same, and also offers other advantages over the prior art and solves other problems associated therewith.

SUMMARY OF THE INVENTION

Accordingly, a hand-actuated retention catheter is provided by the present invention. The hand-actuated retention catheter comprises a tube having outer and inner surfaces, the inner surface defining an inner lumen, an overcoat layer encircling the tube, the overcoat layer having interior and exterior surfaces, a cavity interposed between the tube and overcoat layer, encircling the tube and being defined by portions of the outer surface of the tube and portions of the interior surface of the overcoat layer, and a fluid within the cavity. The overcoat layer includes an "expandable balloon" or expandable balloon section and a "squeeze bulb" or fluid reservoir section interconnected by a "constricting conduit" or catheter sleeve section. The overcoat layer is joined to the outer surface of the tube at distal and proximal ends of the cavity. The cavity includes an expandable balloon portion and a fluid reservoir portion interconnected by a catheter sleeve portion. The catheter sleeve section of the overcoat layer defines a narrowing in the cavity through which fluid passing from the fluid reservoir portion to the expandable balloon portion thereof must pass and preferably includes restriction means for restricting the passage of fluid from the expandable balloon portion to the fluid reservoir portion via the catheter sleeve portion of the cavity, wherein a sufficient amount of the fluid can pass from the fluid reservoir portion, through the catheter sleeve portion, and into the expandable balloon portion when the fluid reservoir portion is compressed, so that the expandable balloon portion of the cavity is enlarged and the outer surface of the overcoat layer proximate the balloon section thereof is also enlarged. Although the catheter sleeve portion of the cavity, and the corresponding catheter sleeve section of the overcoat layer, can have virtually any practical length, for the commercial embodiments presently envisioned, they will preferably have lengths of at least about 0.5 inches, more preferably at least about 1 inch, even more preferably at least about 1.5 inches, and most preferably at least about 2 inches.

It is an object of the present invention to provide a retention catheter including a retention balloon and a hand-actuated mechanism for expanding the retention balloon. This will enable relatively untrained personnel to insert and remove such catheters and may enable patient's to insert and remove them as well. It is also an object of the present invention to provide a retention catheter which provides a safety advantage over presently available balloon catheters. The present catheter includes a certain amount of fluid which can be repositioned in the expandable balloon portion of the cavity so as to expand the balloon section of the overcoat layer. Because the expansion of the balloon section is actuated by compressing the fluid reservoir section of the overcoat layer and the fluid reservoir portion of the cavity, and because that portion of the cavity includes only a limited and predetermined amount of fluid, it is less likely that a user will over inflate the balloon causing it to rupture within the body, when inserted therein.

It is also noted that the catheter sleeve portion of the cavity provides a larger conduit for fluid passing into the balloon portion of the cavity than is ordinarily available in prior art balloon catheters or "Foley" catheters. It will also be appreciated that it will be much more difficult to block this larger conduit, and, consequently, most unlikely that the user will experience any difficulty deflating the balloon when it is time to remove the catheter. Furthermore, if the expandable balloon section of the overcoat layer proves to be difficult to deflate when the catheter is to be removed, it will be easy to obtain access to the fluid reservoir portion of the cavity by puncturing the fluid reservoir section of the overcoat layer which will remain generally outside of the internal passageways of the patient in which the catheter is inserted. This will allow the user to insure that the expandable balloon section can be deflated by manipulating the fluid in the fluid reservoir portion of the cavity.

It is also an object of the present invention to provide a catheter sleeve section of the overcoat layer which provides a constriction between the fluid reservoir portion and the expandable balloon portion of the cavity. The catheter sleeve section is preferably a compliant membrane which can move relatively independently of the tube so as to reduce the tendency for slight movements of the catheter tube to irritate the inner walls of the internal passageway in which the catheter is inserted. Furthermore, the catheter sleeve section, because of its relative independence of movement in respect to the catheter tube, can, in combination with the cushioning effect of the fluid filled catheter sleeve portion of the cavity adjacent thereto, generally comply with the shape of internal passageways through which it passes, thereby reducing the likelihood of any leakage of fluids through such passageways. This is especially true for preferred embodiments which are used as urinary catheters wherein the expandable balloon section is expanded within a person's bladder for retention therein. In such a situation, the adjacent catheter sleeve section, in combination with cushioning activity of the fluid in the adjacent catheter sleeve portion of the cavity, will tend to conform to the shape of the urinary passageway adjacent to the sphincter of the bladder so that leakage through the sphincter and into and through the urinary passageway can be minimized. It will be appreciated that limiting the leakage of urine in this way will greatly reduce the risk of bacterial colonization and infection within the urinary passageway and the bladder itself, by eliminating the opportunity for pools of urine to collect and stagnate within the urinary passageway.

It is a further object of the present invention to provide methods of making the inventive catheters which provide significant cost efficiencies relative to the prior art methods of producing retention catheters. The present device is preferably fabricated primarily of silicone rubber and can be manufactured using an automated system employing a series of coating steps. Although any means of applying the respective coatings may be used, the preferred method employs a series of dipping steps which enable the manufacturer to shape the initial cavity and the overcoat layer, thereby providing the overcoat layer with certain properties which are believed to be desirable in order to provide the retention catheter of the present invention.

These and various other advantages and features of novelty which characterize the present invention are pointed out with particularity in the claims annexed hereto and forming a part hereof. However, for a better understanding of the present invention, its advantages and other objects obtained by its use, reference should be made to the drawings, which form a further part hereof, and to the accompanying descriptive material, in which there is illustrated and described preferred embodiments of the present invention.

BRIEF DESCRIPTION OF THE DRAWINGS

In the drawings, in which like and primed, reference numerals indicate corresponding parts throughout the several views, FIG. 1 is a transverse schematic view of a hand-actuated retention catheter in accordance with the present invention in partial cross-section;

FIG. 2 is a cross-sectional view of the retention catheter shown in FIG. 1 as seen generally from the line 2—2 thereof;

FIG. 3 is a transverse schematic view of a portion of the catheter, as shown in FIG. 1, showing a portion of the fluid in the fluid reservoir portion of the cavity passing through the catheter sleeve portion of the cavity and into the expandable balloon portion of the cavity in response to force exerted upon the fluid reservoir section of the overcoat layer;

FIG. 4 is a cross-sectional view of the retention catheter shown in FIG. 3 as seen generally from the line 4—4 thereof;

FIG. 5 is a view of the retention catheter similar to that of FIG. 3, except that the expandable balloon is in a fully expanded position;

FIG. 14 is a transverse schematic view of the tube shown in FIG. 11-13, but showing only the removable bond-preventing agent in cross-section and only after a portion thereof has been removed from the outer surface of the tube;

FIG. 15 is a transverse schematic view similar to that shown in FIG. 14, but after an additional coating of removable bond-preventing agent has been added to the outer surface of the tube;

FIG. 16 is a transverse schematic view similar to that shown in FIG. 15, but after a further thickness of removable bond-preventing agent is added to the outer surface of the tube;

FIG. 17 is a transverse schematic view similar to that shown in FIG. 16, but after a portion of the removable bond-preventing agent on the outer surface of the tube is removed.

FIG. 19 is a schematic illustration of apparatus used to automate the production of retention catheters in accordance with the present invention similar to that shown in FIG. 1;

FIGS. 20A, 20B and 20C are flow charts disclosing steps of methods of manufacturing retention catheters in accordance with the present invention;

FIG. 21 is a schematic representation of the automated controls for the apparatus shown in FIG. 19, used to automate the production of retention catheters made in accordance with the present invention;

FIG. 22 is a transverse schematic view of an alternate hand-actuated retention catheter in accordance with the present invention in partial cross-section similar to the view shown in FIG. 1;

FIG. 23 is a cross-sectional view of the alternate retention catheter shown in FIG. 22 as seen generally from the line 23—23 thereof;

FIG. 24 is a cross-sectional view of the retention catheter shown in FIG. 22 as seen generally from the line 24—24 thereof;

FIG. 28 is a transverse schematic view of yet another alternate hand-actuated retention catheter in accordance with the present invention in partial cross-section similar to the view in FIG. 1; and FIG. 29 is a cross-sectional view of the alternate retention catheter shown in FIG. 28 as seen generally from the line 29—29 thereof.

DETAILED DESCRIPTION OF THE PREFERRED EMBODIMENTS

Figure 7:
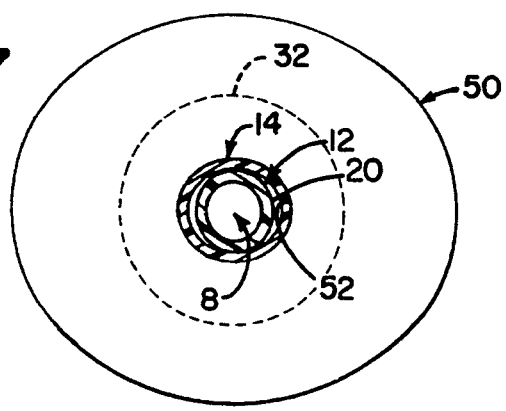
FIG. 7 is a cross-sectional view of the retention catheter shown in FIG. 6, as seen generally from the line 7—7 thereof.

Referring now to the drawings, and specifically to FIGS. 1-9, the present invention provides a hand-actuated retention catheter 5. The retention catheter has an inner lumen 8 defined by an inner surface 10 of a tube 12. The retention catheter 5 further includes an overcoat layer 14 which encircles the tube 12. Interposed between the tube 12 and the overcoat layer 14 is a cavity 16. The cavity 16 contains a fluid 18. The overcoat layer 14 is joined to an outer surface 20 of the tube 12 both above and below the cavity 16 along the length of the tube 12. The cavity 16 includes a fluid reservoir portion 22 and a expandable balloon portion 24, interconnected by a catheter sleeve portion 26 such that fluid 18 can pass between the fluid reservoir portion 22 and the expandable balloon portion 24 via the catheter sleeve portion 26. The overcoat layer 14 includes a fluid reservoir section 30 or "squeeze bulb", an expandable balloon section 32 or "expandable balloon", which are interconnected by a catheter sleeve section 34 or "constricting conduit".

The catheter 5 further includes an eyelet 40 at a distal end 42 of the catheter 5 which communicates with the lumen 8. Preferred embodiments include a plug 44 for closing the lumen 8 at the proximal end 46 of the catheter 5 to limit the unrestrained passage of bodily fluids (not shown) through the lumen 8 and out of the catheter 5. A resilient restriction disc 50 or "washer" encircles the retention catheter 5 proximate the catheter sleeve section 34 of the overcoat layer and distal to the fluid reservoir portion 22 of the cavity 16. The resilient restriction disc 50 provides a mechanism for restricting the passage of fluid 18 between the expandable balloon portion 24 and the fluid reservoir portion 22 of the cavity 16 via the catheter sleeve portion 26 thereof. It will be appreciated that any other restriction device or method for restricting the flow of fluid through a cylindrical passageway may also be used in place of the resilient restriction disc 50 of the present invention. In preferred embodiments, the resilient restriction disc 50 resembles a washer having an inner perimeter 52 which has an inner diameter in its resting state, which is preferably, just slightly less than an outside diameter of the tube 12. The resilient restriction disc 50 will be expanded somewhat about its inner perimeter when it is in its normal engaged state, as shown in FIGS. 1 and 2 when placed on the catheter 5 proximate the constricting conduit 34. Because of its resilient nature, the disc 50 will press the constricting conduit 34 of the overcoat layer 14 up against the outer surface 20 of the tube 12, so that fluid 18 cannot pass through the catheter sleeve portion 26 of the cavity 16 unless forced to do so. Preferably, the force necessary to allow fluid 18 to pass can be applied by squeezing the squeeze bulb 30 before the expandable balloon 32 is expanded, but not by the force exerted by the expandable balloon 32 by itself once it is expanded.

Figure 6:
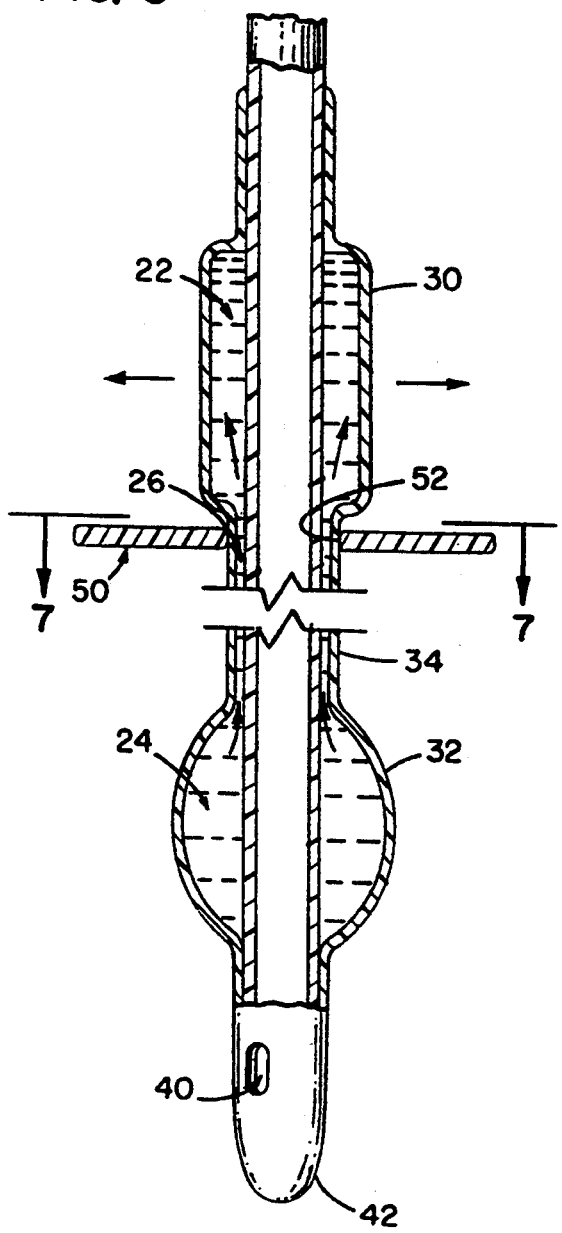
FIG. 6 is a view of the retention catheter similar to that shown in FIGS. 3 and 5, except that a restriction disc for restricting the passage of fluid from the expandable balloon portion of the cavity to the fluid reservoir portion of the cavity via the catheter sleeve portion thereof has been manipulated to allow fluid to flow from the expandable balloon portion to the fluid reservoir portion under the pressure of the resilient expandable balloon section of the overcoat layer.
Figure 8:
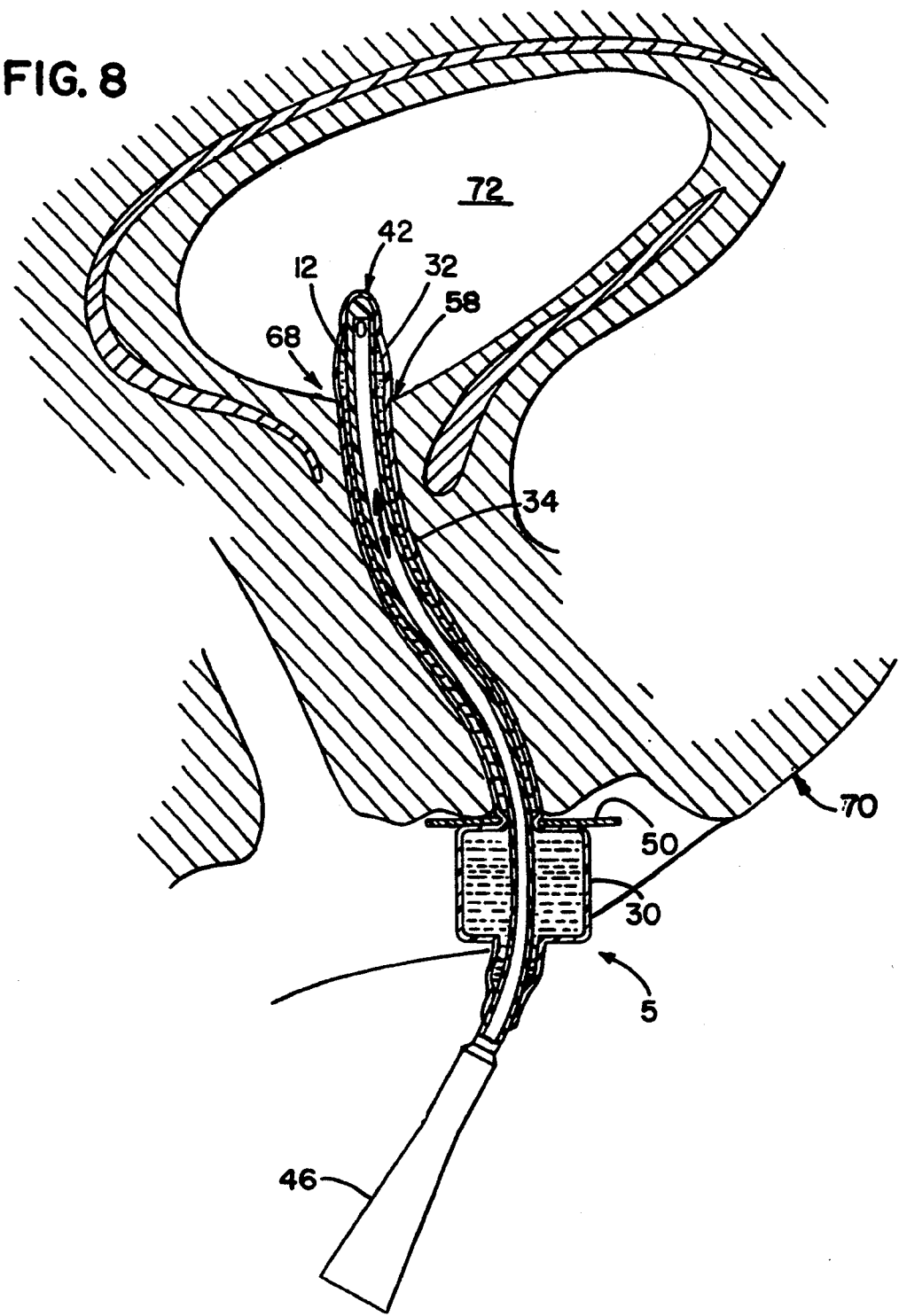
FIG. 8 is a transverse schematic sectional view showing a partial cross-section of a catheter similar to the retention catheter shown in FIG. 1 when inserted in a urethral tract of a patient, but prior to expansion of the expandable balloon.
Figure 9:
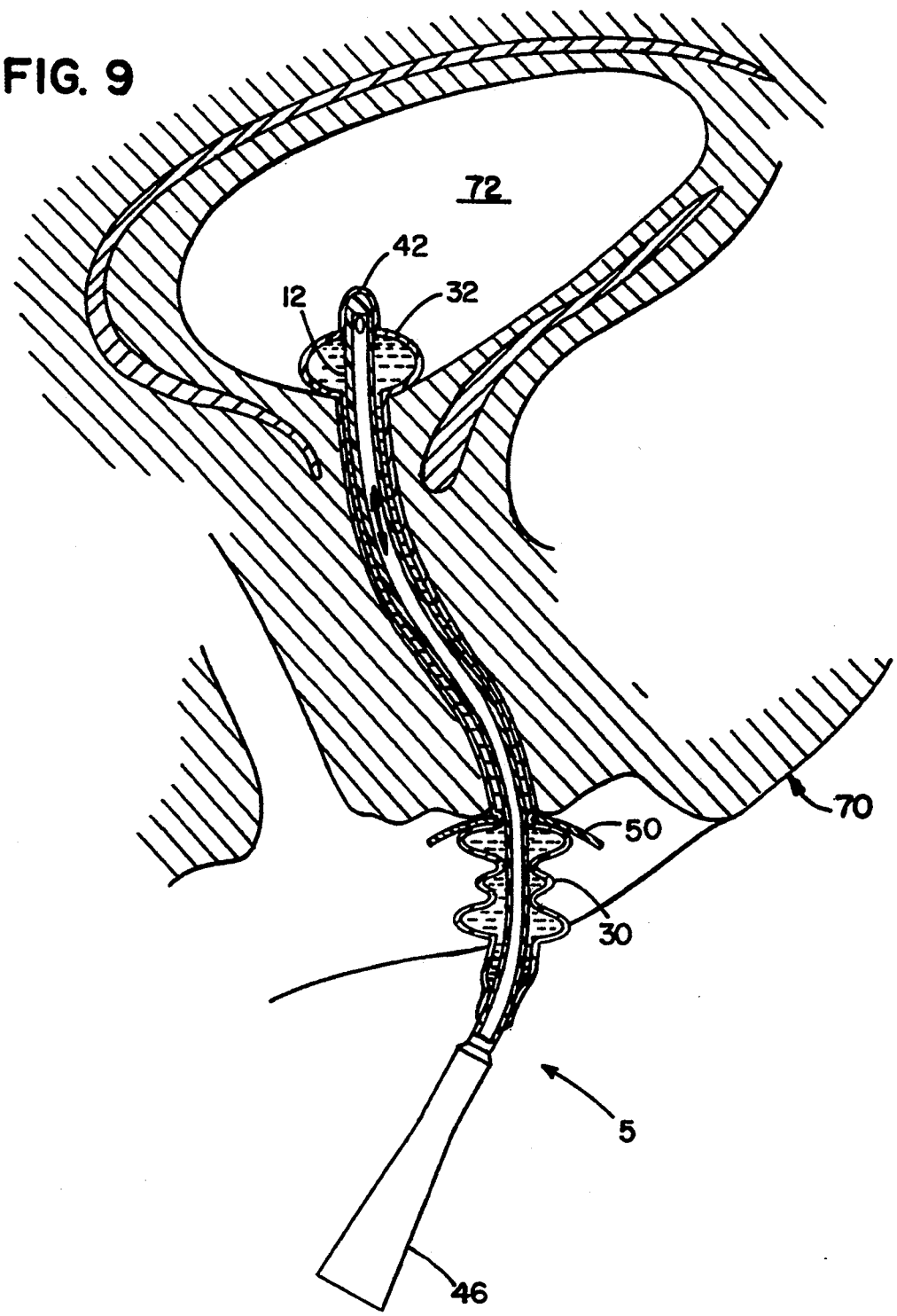
FIG. 9 is a view similar to that shown in FIG. 8, except that the "squeeze bulb" of the retention catheter has been compressed and the expandable balloon has been fully expanded.

In FIGS. 1 and 2, the restriction disc 50 is shown in its normal engaged state, wherein the disc 50 encircles the catheter sleeve section 34, thereby restricting the passage of fluid 18 through the catheter sleeve portion 26 of the cavity 16. In order to expand the expandable balloon portion 24 of the cavity 16 and the expandable balloon section 32 of the overcoat layer 14, the squeeze bulb can be compressed by hand to force a portion of the fluid 18 in the fluid reservoir portion 22 of the cavity 16 through the catheter sleeve portion 26 and into the expandable balloon portion 24. By compressing the fluid reservoir portion 22 of the cavity 16, sufficient force can be placed on a narrowing of the constricting conduit 34 proximate the disc 50 to enlarge the resilient inner perimeter 52 of the restriction disc 50 enough to permit fluid 18 to pass through the catheter sleeve portion 26, thereby allowing the balloon portion 24 to be expanded as shown in FIGS. 3 and 4. When fully expanded in this way, the balloon 32 will provide a bulbous enlargement at the distal end 42 of the catheter 5 which is generally effective to prevent the removal of the retention catheter 5 from an internal passageway 68 in which the retention catheter 5 is positioned (see also FIGS. 8 and 9). Once the expandable balloon portion 24 of the cavity 16 and the expandable balloon section 32 of the overcoat layer 34 have been fully expanded, as shown in FIGS. 5 and 9, the balloon 32 can be "deflated" or returned generally to its normal, unexpanded state, generally shown in FIGS. 1 and 8 by grasping opposite sides of the resilient restriction disc 50 and pulling them in opposite directions so that fluid 18 can pass through the catheter sleeve portion 26 of the cavity 16 as shown in FIGS. 6 and 7. By grasping the disc 50 on opposite sides and pulling in opposite directions, the resilient disc 50 can be deformed so as to pull the inner perimeter 52 away from the tube 12 on opposite sides of the tube 12 so that the constricting conduit 34 is not fully engaged with the entire circumference of the outer surface 20 of the tube 12, and the fluid 18, driven by the force of the resilient, expandable balloon 32, flows into the fluid reservoir portion 22 of the cavity 16. Because the expandable balloon section 32 of the overcoat layer 14 is made of a resilient polymeric material, preferably silicon rubber, the expandable balloon portion 24 of the cavity 16 will be compressed by the force exerted by the expandable balloon section 32 when the resilient restriction disc 50 is manipulated to permit fluid 18 to pass through the catheter sleeve portion 26 of the cavity 16. In this way, the expandable balloon section 32 can generally return to its normal, unexpanded state and fluid 18 can generally return to the fluid reservoir portion 22. Once the expandable balloon section 32 is returned to its normal unexpanded state, as shown generally in FIG. 8, the retention catheter 5 can then be easily removed from the internal passageway 68 in which it resides.

Referring now also to FIG. 10–19, certain preferred methods of making the preferred hand-actuated retention catheter 5 (shown in FIG. 1) are described. These catheters 5 are made of silicone rubber, although it will be appreciated that other suitable polymeric materials may be used to make the present invention.

Figure 10:
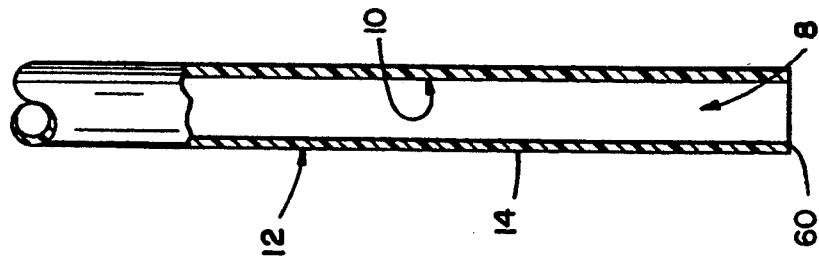
FIG. 10 is a transverse schematic view of a tube in partial cross-section which is used to make the retention catheter shown in FIG. 1.

Referring now initially to FIG. 10, a resilient, polymeric tube 12, preferably a silicone rubber tube 12, is provided. Although such a tube 12 can be provided by extruding a ribbon of polymeric tubing and cutting the tubing into desired lengths, in the Applicants' initial manufacturing efforts, commonly available medical grade silicone rubber tubing has been purchased and then cut into desired lengths.

Figure 11:
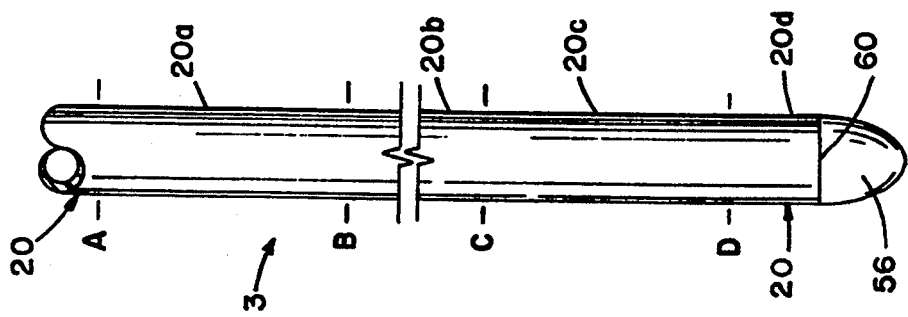
FIG. 11 is a transverse schematic view of the tube shown in FIG. 10 following the addition of a tip at the distal end thereof.
Figure 12:
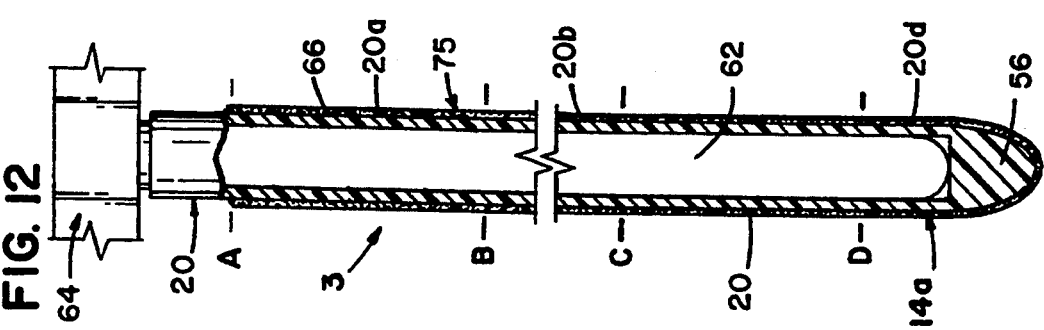
FIG. 12 is a partial cross-sectional view of the tube shown in FIG. 11 when secured upon one of a plurality of support rods on a moveable pallet, and following the addition of a coating of a removable bond-preventing agent to a portion of the outer surface of the tube.
Figure 13:
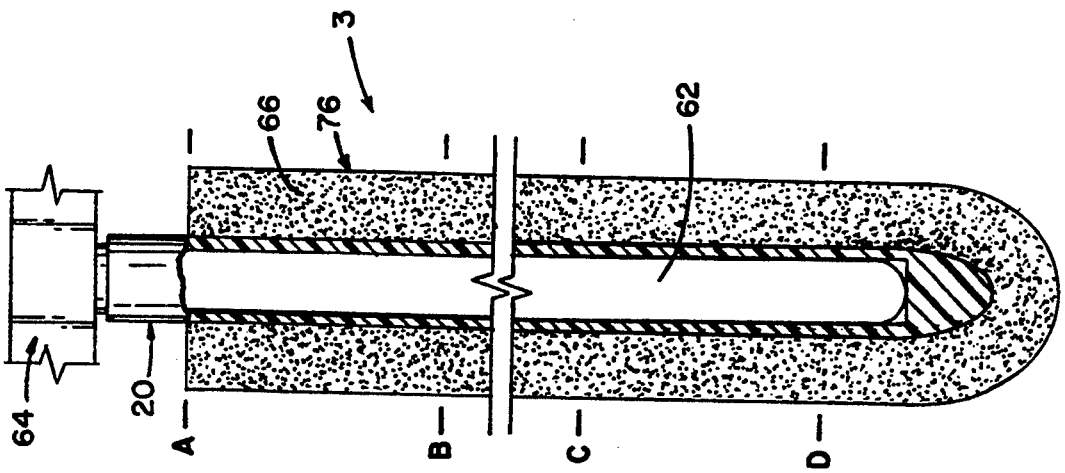
FIG. 13 is a view similar to that shown in FIG. 12, but after the addition of an additional thickness of the removable bond-preventing agent to the outer surface of the tube.

Referring now also to FIG. 11, once cut into desired lengths, a polymeric tip 56 is secured, preferably molded, to the distal end 60 of the tube 12 to close off the lumen 8 at the distal end 60 and thereby create an intermediate tube 3. The tip 56 is preferably added by inserting the tube 12 in a mold (not shown) or a tip-forming device (not shown), in which a desired amount of uncured silicone rubber is injected to form the tip once the tube 12 is inserted therein. The uncured silicone rubber will preferably be a self-leveling RTV (room temperature vulcanizing) silicone rubber such as Dow Corning 734 Self Leveling RTV Silicone rubber from Dow Chemical, Midland, Mich. Presently, the Applicants use an intermediate tube 3 made in this way. It is envisioned, however, that a preferred process may be developed wherein the entire intermediate tube 3, including the tube 12 and a tip similar to tip 56 will be made by dipping a mandrel (not shown) in a suitable polymeric material in a manner which is effective to create the intermediate tube 3. Any other convenient methods for securing a tip to the tube 12 may also be used.

Referring now also to FIGS. 12–21, the intermediate tube 3 is secured to a support rod 62 on a moveable pallet 64. FIG. 19 provides a schematic representation of a preferred mechanized catheter production line 81 which is virtually fully automated. The mechanized production line 81 includes one or more pallets 64 having a plurality of support rods 62. The moveable pallet 64 is attached to a transport mechanism 82 which can move the pallet to a position over one of a plurality of dip tanks 84, 86, 88, 90, 92, 94. Each of the respective dip tanks will contain a fluid in which intermediate catheters 3 secured upon respective support rods 62 are immersed when the respective dip tank is raised. Movement of the pallet 64 is controlled by an output from a computer control mechanism 83, illustrated schematically in FIG. 21, which are directed to the transport mechanism 82. Each of the respective dip tanks 84, 86, 88, 90, 92, 94 are raised and lowered by associated lift mechanisms. The lift mechanisms are also controlled by outputs from the computer control mechanism 83. Each of the lift mechanisms includes a speed control capable of modulating the rate at which the respective dip tank is raised and lowered so that the speed at which the respective intermediate tubes 3 are immersed into and withdrawn from the respective fluid within the respective dip tank can be varied. The computer control mechanism 83 also receives inputs from depth sensors within each of the respective dip tanks. The depth sensors, preferably ultrasonic depth sensors, are capable of providing an input to the computer control mechanism 83 which enables the computer control mechanism to determine when the intermediate tubes 3 are immersed to a desired depth in the respective dip tank. Timers are also provided for each of the respective dip tanks in order to provide inputs to the computer control mechanism 83 so that the computer control mechanism 83 can determine when a desired period of time has elapsed. A computer program is provided which moves the pallet along the mechanized production line 81 and raises and lowers the respective dip tanks at predetermined times, at predetermined rates of speed, and to predetermined locations and/or heights to enable the mechanized production line 81 to produce a plurality of completed intermediate catheters 4 from the intermediate tubes 3 secured to the respective support rods 62. In alternate embodiments, the mechanized production line 81 may have a series of pallets (not shown) which are moved along an alternate transport mechanism (not shown) in series.

The moveable pallet 64 will preferably have a plurality of support rods 62 to accommodate a plurality of intermediate tubes 3. In alternate embodiments, a tube 12 can be secured to the support rod 64, and subsequently dipped in polymeric material in a manner sufficient to add a polymeric tip 56 so as to created an intermediate tube 3.

The intermediate tube 3 is then coated with a removable bond-preventing agent 66, preferably petroleum jelly or petrolatum, which forms a first coating 75 covering first, second, third, and fourth portions 20a, 20b, 20c and 20d of the outer coating 20 of the intermediate tube 3. This is preferably accomplished by dipping the intermediate tube into a bath of heated petroleum jelly or petrolatum. Additional removable bond-preventing agent 66 is then coated onto the first coating 75 to form a second coating 76. This second coating 76 is preferably much thicker than the first coating 75. Portions of the second coating 76 are then stripped off of the second, third, and fourth portions 20b, 20c, and 20d of the outer surface 20, and a third coating 77 of removable bond-preventing agent 66 is placed on the second, third, and fourth portions 20b, 20c, and 20d of the outer surface 20. A fourth coating 78 is then added proximate the third and fourth portions 20c and 20d of the outer coating 20 over the third coating 77. The third and fourth coatings 77 and 78 of removable bond-preventing agent 66 coating the fourth portion 20d of the outer surface 20 are then removed, and the outer surface 20 of the intermediate tube 3 and the remaining portions of the second, third, and fourth coatings 76, 77, and 78 of removable bond-preventing agent 66 covering the first, second, and third portions 20a, 20b, and 20c of the outer surface 20, respectively, are coated with a suitable polymeric material, preferably silicone rubber, which adheres to the outer surface 20 of the intermediate tube 3 above the first portion 20a thereof and below the third portion 20c, and creates an overcoat layer 14 having an exterior surface 36.

Although the present hand-actuated retention catheter 5 can be constructed of any suitable, medically acceptable, polymeric material, medical grade silicone rubber is preferred. It will be appreciated that such a silicone rubber polymeric must be fully cured prior to sale or use. In the preferred methods of making the present hand-actuated retention catheter 5, the intermediate tube 3 is dipped into a bath of uncured silicone rubber to form the overcoat layer 14. Following this step, the overcoat layer 14 is air-dried and subsequently cured to form a completed intermediate catheter 4, such as that shown in FIG. 18. The overcoat layer 14 of the completed intermediate catheter 4 is then cured and removed from the pallet 64. The completed intermediate catheters 4 are then, preferably, further cured and then soaked in a bath of hot mineral oil for several hours. In the preferred embodiment, the mineral oil will diffuse through the overcoat layer 14 and into the petrolatum in the cavity 16, and the petrolatum will diffuse out of the cavity into the hot mineral oil. The remaining fluid 18 in the cavity 16 will be a mineral oil/petrolatum fluid having a significantly lower viscosity than petrolatum at room temperature. A different fluid such as water, sterile saline, glycerin, polyethylene glycol, and the like, or mixtures thereof may also be substituted for the mineral oil/petrolatum fluid in alternate embodiments by removing most of the latter fluid, and then inserting the former by any appropriate means.

An eyelet 40 is then punched through the overcoat layer 14 and the tube 12 proximate the fourth portion 20d of the outer surface 20, in order to provide an opening which communicates with the lumen 8 from the outside of the intermediate catheter 4. An end piece 80 is then secured to the proximal end 61 of the intermediate catheter 4 to form a completed hand-actuated retention catheter 5, and the completed retention catheter 5 is tested.

Figure 18A:
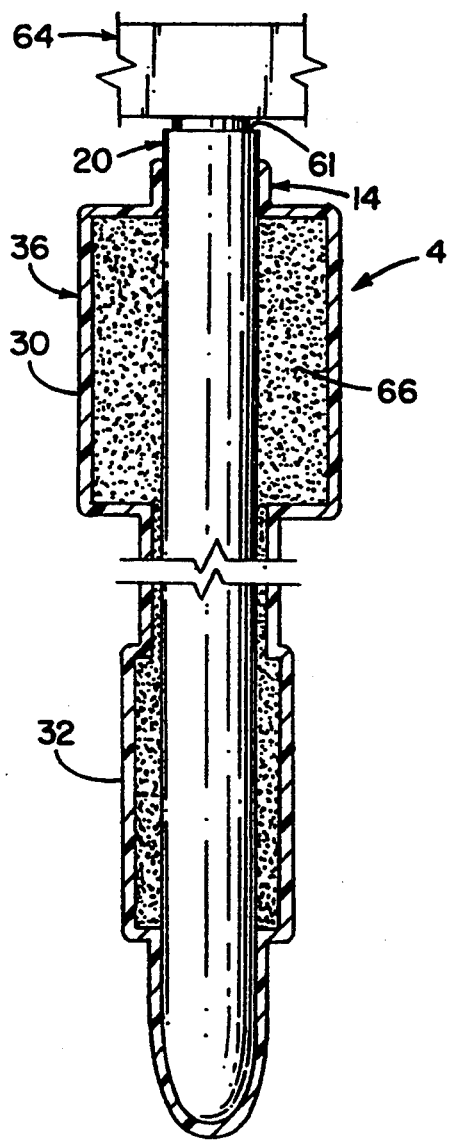
FIGS. 18A and 18B are transverse schematic views similar to that shown in FIG. 17, but showing an overcoat layer on the outer surface of the tube.
Figure 18B:
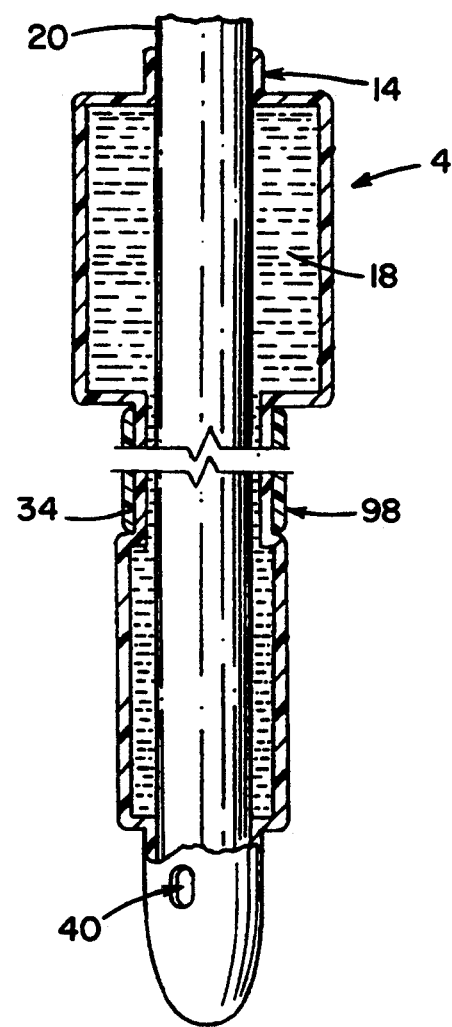

During the testing of the completed retention catheter 5, a removable cylindrical support device 98 is secured around the catheter sleeve section 34 of the overcoat layer 14 adjacent to the expandable balloon section 32, as shown in FIG. 18B, to minimize any potential expansion of the catheter sleeve section 34. In this way, when the fluid reservoir section 30 is compressed, and the expandable balloon section 32 is expanded for the first time, the catheter sleeve section 34 will only be allowed to expand minimally, if at all, because the removable cylindrical support device 98 prevents, or at least minimizes, expansion of the catheter sleeve section 34. It has been observed that, once the expandable balloon section 32 of the overcoat layer 14 has been initially expanded in this way, it is easier to expand the expandable balloon 32 in subsequent attempts. On the other hand, since the catheter sleeve section 34 of the overcoat layer has not been stretched to the same degree, it will be more resistant to expansion or stretching than the expandable balloon 32 in subsequent attempts. Therefore, the step of initially expanding the balloon section 32, helps to create a retention catheter 5 which has a readily expandable balloon section 32, as opposed to the catheter sleeve section 34 which does not expand as readily upon compression of the fluid reservoir section 30.

Following the testing of the expandable balloon 32, the expandable restriction disc 50 is secured onto the retention catheter 5 by slipping the distal end 42 of the catheter 5 through the disc 50 until the disc 50 encircles the catheter 5 proximate the catheter sleeve section 34 of the overcoat layer 14 just distal to the squeeze bulb 30.

Referring now to FIGS. 6, 7, 8 and 9, during use, the hand-actuated retention catheter 5 of the present invention is inserted into a urinary passageway 68 of a patient 70 until the expandable balloon section 32 is positioned within the patient's bladder 72. In preferred embodiments, the catheter sleeve section 34 of the overcoat layer will be about 0.5 to about 3.5, preferably about 1.5 to about 2.5, more preferably about 2 inches long for insertion into the urinary passageway 68 of a female patient. When the length of the preferred catheter sleeve section 34 is the same as that of such a female patient's urinary passageway, the distal end 42 and the catheter sleeve section 34 of the retention catheter 5 are inserted until the expandable restriction disc 50 and the squeeze bulb limit further insertion into the urinary passageway 68. The expandable balloon 32 is then expanded by grasping the squeeze bulb 30 and squeezing it to compress the fluid reservoir portion 22 of the cavity 16, thereby providing enough force to drive the fluid 18 through the catheter sleeve portion 26 of the cavity 16 and into the expandable balloon portion 24 thereof. The expandable balloon 32 will then expand, and the inner perimeter 52 of the expandable restriction disc 50 will subsequently force the catheter sleeve section 34 of the overcoat layer 14 against the outer surface 20 of the tube 12 about an entire circumference thereof, so that the fluid 18 cannot return to the fluid reservoir portion 30 and the expandable balloon 32 will remain in its fully expanded state.

When the expandable balloon 32 is in its fully expanded state (as shown in FIG. 9), the retention catheter 5 will be secured within the urinary passageway 68 because the expandable balloon 32 will be larger than the normal opening in the urinary passageway 68 proximate the sphincter 58 at the distal end of the bladder 72. In order to remove the retention catheter 5 from the urinary passageway 68, a user will grasp opposite sides of the expandable restriction disc 50 and pull in opposite directions, thereby deforming the restriction disc 50 in a manner similar to that shown in FIG. 7. If sufficient force is used, the inner perimeter 52 of the restriction disc 50 can be pulled away from the outer surface 20 of the tube 12 on opposite sides thereof, so that fluid can pass through the catheter sleeve portion 26 of the cavity 16 under pressure created by the resilient overcoat layer 14 which is expanded proximate the expandable balloon 32. The force generated by the expandable balloon 32 will preferably be sufficient to push sufficient fluid 18 out of the expandable balloon portion 24 of the cavity 16 so that the expandable balloon 32 generally returns to its normal unexpanded state, similar to that shown in FIG. 1, and the retention catheter 5 can be withdrawn from the bladder 72 and the urinary passageway 68 without difficulty.

If, for some reason, the fluid 18 does not automatically flow back into the fluid reservoir portion 26 of the cavity 16 when the restriction disc 50 is deformed, as described hereinabove, it is possible to remove the restriction disc 50 entirely and even puncture the overcoat layer 14 proximate the squeeze bulb 30 to allow the fluid 18 to drain out of the cavity 16. Alternatively, further compression of the squeeze bulb 30 may urge sufficient additional fluid 18 through the catheter sleeve portion 26 of the cavity 16 to dislodge any obstruction therein which may otherwise prevent the fluid 18 from flowing out of the expandable balloon portion 24 and back into the fluid reservoir portion 22.

The expandable restriction disc 50 of the present invention may be made of any resilient polymeric material. In preferred embodiments, however, the restriction disc 50 will be made of silicone rubber. The overcoat layer 14 of the present retention catheter 5 preferably has a thickness less than the thickness of the tube 12 between its outer surface 20 and its inner surface 10. In preferred embodiments, the thickness of the overcoat layer 14 will be about 0.010 to about 0.030, preferably about 0.015 to about 0.025, more preferably about 0.017 to about 0.023, most preferably about 0.020 inches (about 0.05 cm). The thickness of the tube 12 will be comparable to that of the tube in Applicant's prior applications incorporated herein by reference. The overcoat layer 14 is preferably very soft and compliant, and will move relatively independently of the tube 12. For instance, when the proximal end 46 of the retention catheter 5 is either twisted, pushed, or pulled while positioned within the urinary passageway 68 of the patient 70, the tube 12 can twist, and move inward and outward in respect to the passageway 68 with a significant degree of independence of the overcoat layer 14, which will stretch and twist in response to such movements, but necessarily be compelled to move relative to its position within the internal passageway 68 in response to such movements. It will be appreciated that this will reduce the amount of irritation caused by the exterior surface 36 of the retention catheter 5, because this relative independence of the respective elements of the catheter will allow structural portions of the catheter 5 to move independently of the exterior surface 36, which is most likely to be in contact with internal surfaces of the respective passageways in which the catheter 5 is inserted. It will also be appreciated that the advantages this will afford are analogous to the advantages set forth in U.S. patent application Ser. No. 07/487,422, filed Mar. 1, 1990, the disclosure of which is incorporated herein by reference. It will be further appreciated that the present invention provides additional advantages over the catheters disclosed therein, because the catheter sleeve section 34 hereof is secured only to the adjacent sections of the overcoat layer 14 and not to the tube 12. This is believed to provide even more independence of movement to the tube 12 and the other structural portions of the retention catheter 5 which are resiliently interconnected with the catheter sleeve section 34.

In the Applicants' use of the preferred methods of the present invention, catheter production is almost completely automated. Sets of catheters 5 are manufactured simultaneously. The preferred pallet 64 has 400 spring steel support rods 62 attached to the pallet in 20 rows of 20 rods, wherein each of the rods 62 is about 1 inch from each adjacent rod. Tubing (not shown) can be either purchase or made by an extrusion process known to those of skill in the art. The tubes 2 are cut to length, tipped and secured on the pallet 64.

In a preferred embodiment of the present method, 400 of the intermediate tubes 3 are mounted vertically on rigid spring steel support rods 62 on a moveable pallet 64. The pallet 64 is then moved via a transport mechanism 82 (see FIG. 19) over a series of dip tanks 84, 86, 88, 92, 94, 96 as follows in one of these embodiments:

(A) The pallet 64 is stopped over a first tank 84, which contains a liquid petrolatum mixture at about 125° F. (about 52° C.). The mixture is the preferred removable bond-preventing agent 66. The mixture will include 45% Perrecta ™ Petrolatum USP (from Sonneborn Petrolatums, Sonneborn Div., Witco Chemical Corp., New York, N.Y.); 45% Mineral Jelly No. 17 (from Sonneborn Petrolatums); and 10% Parafin (Amoco ESKAR ™ wax, Amoco Oil Co., Chicago, Ill.). The tank is raised so as to immerse the intermediate tubes 3 into the petrolatum to such a depth (up to dashed line A shown in FIGS. 12 and 13) that the petrolatum coats the first, second, third and fourth portions 20a, 20b, 20c and 20d of the outer surface 20. The dip tank 84 is then lowered and these portions of the outer surface 20 of the intermediate tubes 3 are coated with a first coating 75 of petrolatum. The tubes 3 are allowed to air dry for about 30 seconds, and the dip tank is raised again and the tubes 3 are immersed again to the same depth. This is repeated 48 times until a second petrolatum coating 76 is completed which is very thick (see FIGS. 12 and 13).

(B) The pallet 64 is then automatically advanced and stopped over a second dip tank 86 which contains hot USP petrolatum heated to about 180° F. (about 82° C.). The second dip tank 86 is raised so as to immerse the intermediate tubes 3 into the super-heated petrolatum for 1 minute so that the super-heated petrolatum comes up to dashed line B and into contact with the second petrolatum coating 76 on the second, third and fourth portions 20b, 20c and 20d of the outer surfaces 20 of the intermediate tubes 3 from the prior dipping step. The second dip tank 35 is then lowered. This dipping step causes the coating 77 of petrolatum from the prior dipping step to be largely removed from the second, third and fourth portions 20b, 20c and 20d of the outer surface 20 of the intermediate tubes 3, as shown in FIG. 14. Some residual petrolatum may remain on these portions of the outer surface 20. However, most of the petrolatum is removed from them.

(C) The pallet 64 is then automatically advanced and stopped over a third dip tank 88 containing a liquid petrolatum mixture identical to that in the first dip tank 84, except that the temperature is about 135° F. (about 57° C.). The third dip tank 88 is then raised so as to immerse the intermediate tubes 3 into the petrolatum mixture to the same depth as they were immersed in the super-heated petrolatum in the second dip tank 86. The tank 88 is then lowered, leaving a third coating 77 of petrolatum on the second, third and fourth portions 20b, 20c and 20d of the outer surface 20, as shown in FIG. 15. The tubes are then immersed twice again up to the dashed line C and a fourth coating 78 is created over the third and fourth portions 20c and 20d of the outer surface 20 (as shown in FIG. 16) which is roughly 3 times as thick as the third coating 77, but not nearly as thick as the second coating 76.

(D) The pallet 64 is then automatically advanced and stopped over a fourth dip tank 90 containing hot USP petrolatum like that in the second dip tank 86. The fourth dip tank 90 is raised and the tubes 3 are immersed in the super-heated petrolatum up to the dashed line D for about 30 seconds. The fourth dip tank is then lowered and the fourth coating 78 of petrolatum is removed from the fourth portion 20d of the outer surface 20, as shown in FIG. 17.

(E) The pallet 64 is then automatically advanced and stopped over a fifth dip tank 92 containing a volatile organic solvent such as toluene, trichloromethane or the like. The fifth tank 92 is then raised to immerse the intermediate catheters 3 in the organic solvent up to dashed line D so as to remove any remaining petrolatum 66 on the fourth portion 20d of the outer surface 20. The intermediate catheter tubes 3 now have three bands 76, 77 and 78 of semi-solid petrolatum around the axial circumference of each of the intermediate tubes 3, as shown in FIG. 17.

(F) The pallet 64 is then lowered, and the organic solvent is allowed to evaporate from the outer surface 20 for about 15 minutes. The pallet 64 is then automatically advanced to a sixth dip tank 94 containing a hexamethyl disiloxane silicone rubber mixture which is effective to minimize any disruption of the integrity of the petrolatum coatings 76, 77 and 78 remaining on the intermediate tubes 3. The preferred silicone rubber mixture is a 50-50 mixture of uncured silicone rubber in hexamethyl disiloxane. This mixture includes 12 parts by weight of silicone rubber No. 4850 (6 parts part A, 6 parts part B) from Dow Corning; 12 parts by weight of silicone rubber No. 4720 (6 parts part A, 6 parts part B) from Dow Corning; 64 parts by weight of hexamethyl disiloxane; and 2 parts by weight of Xylene. The sixth dip tank 94 is then raised to immerse essentially the entire length of the intermediate tube 3 in the silicone mixture. This step is subsequently repeated 7 times at 8-minute intervals to allow time for significant solvent evaporation. A preferred thickness of the resulting overcoat layer 14 is about 17.5 thousandths of an inch (plus or minus about 2.5 thousandths of an inch). When the tank 94 is lowered for the last time, the overcoat layer 14 is allowed to dry and the solvent is allowed to evaporate for about 30 minutes, preferably about an hour.

(G) In a preferred embodiment of the present method, the pallet 24 is advanced to yet another dip tank (not shown) similar to the others, but containing hot USP petrolatum, heated to about 170° F. (about 77° C.). The tubes 3 are completely immersed in the hot petrolatum for 1 hr to cure the uncured silicone rubber and form the completed intermediate catheters 4 shown in FIG. 18A, and the tank (not shown) is then lowered.

(H) The completed intermediate catheters 4 are then removed from the pallets and further cured in hot air at 220° F. (about 104° C.) for about an hour and a half (1.5 hrs).

(I) After the completion of the heat cure, the intermediate catheters 4 are allowed to cool and end pieces 80 are attached to the proximal ends 61 of each of the intermediate catheters 4, and an eyelet 40 is created to form the completed hand-actuated retention catheter 5. Alternatively, the intermediate catheters are soaked in hot mineral oil at 200° F. (93° C.) for 24 hours. The intermediate catheters 4 are then removed from the oil, cleaned and end pieces 80 are attached thereto, and an eyelet 40 is created to form the completed catheters 5.

(J) The completed Foley catheters 5 are finished by punching the fluid conduit access opening or eyelet 40 in the exterior surface 36 such that it communicates with the fluid conduit lumen 8 in a location below or distal to the expandable balloon section 32.

(K) If not previously soaked in mineral oil, the completed Foley catheters 5 are then soaked for 24 hrs in a hot bath of mineral oil at 200° F. (about 93° C.). The mineral oil will generally replace the petrolatum 66 in the cavity 16 after this period of time, and will remain a fluid 18 at room temperature.

(L) The expandable balloon section 32 is then tested and stretched, and the catheters 5 are packaged and then sterilized prior to shipment.

Figure 20B:
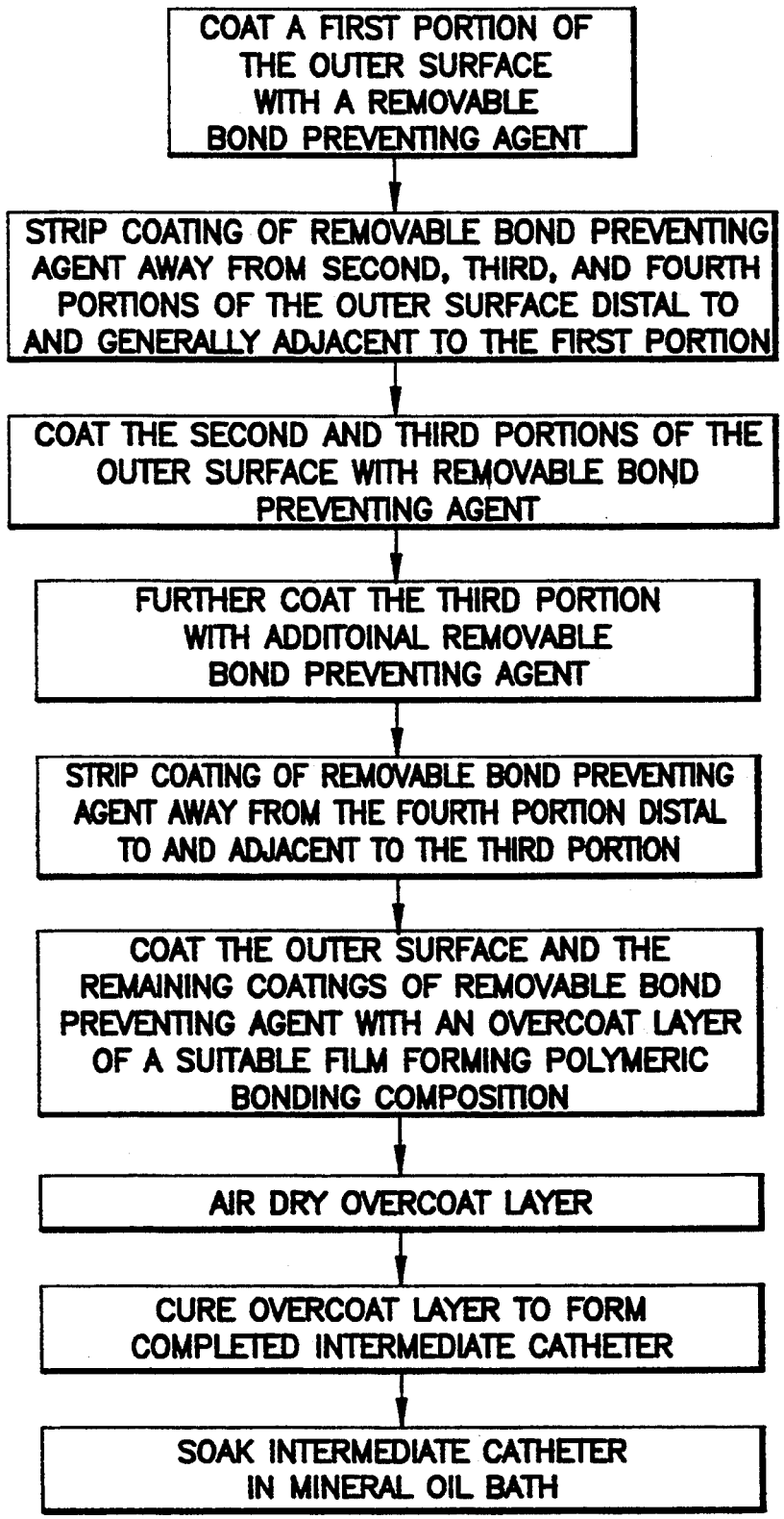
Figure 25:
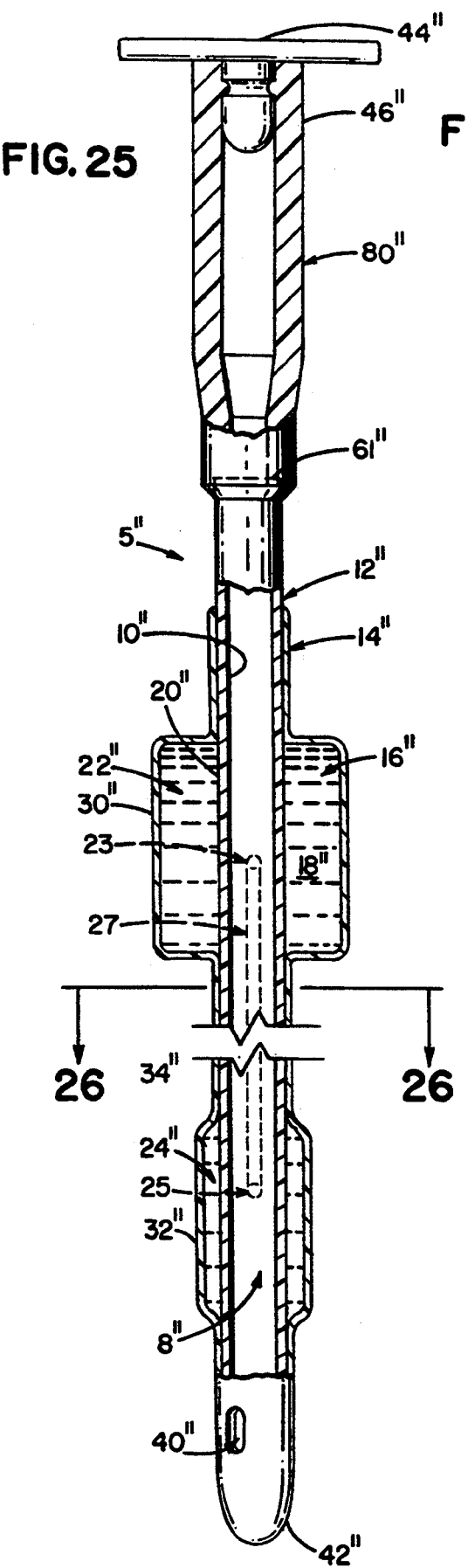
FIG. 25 is a transverse schematic view of another alternate hand-actuated retention catheter in accordance with the present invention in partial cross-section similar to the view shown in FIG. 1.
Figure 26:
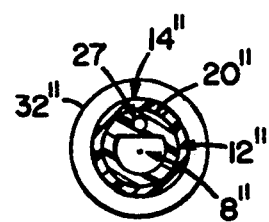
FIG. 26 is a cross-sectional view of the alternate retention catheter shown in FIG. 25 as seen generally from the line 26—26 thereof.

Referring now to FIGS. 20a, 20b and 20c, the present invention provides a method of making hand-actuated retention catheters 5 including the following steps:

(A) Providing a tube having inner and outer surfaces, the inner surface defining an inner lumen;

(B) Cutting the tube to a desired length;

(C) Putting a tip on the distal end of the tube, thereby sealing off the inner lumen;

(D) Securing the tube to a moveable pallet.

These steps are followed by the following steps:

(A) Coating a first portion of the outer surface with a removable bond preventing agent;

(B) Stripping the coating of removable bond preventing agent away from the second, third and fourth portions of the outer surface generally adjacent to the first portion thereof;

(C) Coating the second, third and fourth portions of the outer surface with a further coating of removable bond preventing agent;

(D) Further coating the third portion of the outer surface with the removable bond-preventing agent;

(E) Stripping the coating of bond-preventing agent from the fourth portion of the outer surface;

(F) Coating the outer surface and the remaining coatings of removable bond-preventing agent with an overcoat layer of a suitable film forming polymeric bonding composition;

(G) Air drying the overcoat layer;

(H) Curing the overcoat layer to form the completed intermediate catheter; and (I) Soaking the intermediate catheter in a hot mineral oil bath (200° F.) for 24 hrs.

Following those steps, methods of the present invention include the following steps:

(A) Punching a fluid conduit lumen access opening or eyelet in the distal end of the intermediate catheter to communicate with the inner lumen;

(B) Securing an end piece to the proximal end of the intermediate catheter to form a completed retention catheter;

(C) Testing the balloon portion of the resulting retention catheter;

(D) Packaging the resulting retention catheters; and (E) Sterilizing the retention catheters.

The automated system that Applicants claim will permit completed catheters 5 to be manufactured at the rate of about 1,600 catheters per hour. Because little hand-work is involved, the catheters 5 produced will be consistent, of very high quality, and more cost-effective than comparable prior art catheters. The exterior surface 36 is believed to be smoother than the exterior surface of hand-glued balloons.

The present invention also includes a method of making a silicone rubber catheter 5 having an overcoat layer 14 enclosing a cavity 16 on an outer surface 20 of an inner tube 12, wherein the cavity 16 separates the overcoat layer 14 from the inner tube 12. The method includes providing a silicone rubber tube 12. Initially coating portions of an outer surface of the silicone rubber tube 12 with a bond preventing agent 66 in a plurality of dipping steps, wherein the tube 12 is immersed into the bond preventing agent 66 to a desired depth for a desired length of time, and subsequently removed. The plurality of dipping steps are automated in series by the mechanized catheter production line 81 which includes a computer control mechanism 83. The desired depth and/or the length of time for each of the plurality of dipping steps is prescribed so that a residual coating of bond preventing agent remains on portions of the silicone rubber tube 12 following the plurality of dipping steps. The residual coating has a variable thickness as a result of a variation between the number of dipping steps, the depth, and/or the length of time of any two of the plurality of dipping steps. And, subsequently coating the silicone rubber tube 12 and the residual coating of bond preventing agent 66 with a polymeric bonding composition containing silicone rubber to form a shaped overcoat layer 14 wherein the shape of the overcoat layer 14 results in part from the variable thicknesses of the residual coating.

A step of initially coating preferably includes stripping the tube, wherein the tube is immersed in a stripping fluid to a desired depth for a desired length of time in order to remove at least a portion of the bond preventing agent from the outer surface 20 of the silicone rubber tube 12. Preferably, the overcoat layer 14 of the catheter 5 is shaped to include a bulbous balloon section 32 distal to a cylindrical sleeve section 34 interconnected therewith, wherein the thickness of the residual coating of bond preventing agent 66, during the step of subsequently coating, is greater in a region proximate the bulbous balloon section 32 than it is in a region proximate the cylindrical sleeve section 34. In preferred embodiments, the overcoat layer 14 is shaped to include an enlarged cylindrical fluid reservoir section 30 interconnected with and separated from the bulbous balloon section 32 by the cylindrical sleeve section 34. The thickness of the residual coating of bond preventing agent 66, during a step of subsequently coating, is preferably lesser in a region proximate the cylindrical sleeve section 34 than it is in regions proximate either the cylindrical fluid reservoir section 30 or the bulbous balloon section 32. Preferably, the polymeric bonding composition is an uncured silicone rubber composition and the step of subsequently coating is followed by a step of curing the uncured silicone rubber composition in the overcoat layer 14.

It is envisioned by the present Applicants that certain patients having a urinary passageway 68 which narrows significantly proximate the urinary sphincter or the neck of the bladder may have difficulty using the present hand-actuated retention catheter 5. This is because the narrowing of the urinary passageway 68 proximate the neck of the bladder may force the catheter sleeve section 34 of the overcoat layer 14 up against the outer surface 20 of the tube 12 within the catheter sleeve portion 26 of the cavity 16 so that fluid is not able to pass out of the expandable balloon portion 24 of the cavity 16 once that portion of the cavity 16 has been expanded with fluid 18 from the fluid reservoir portion 22. It will be appreciated that it may be difficult to remove the retention catheter 5 if this occurs, because the narrowness of the urinary passageway 68 will prevent the fluid 18 from leaving the expandable balloon portion 24 of the cavity 16 even when the disc 50 is deformed in a way which would otherwise allow fluid 18 to pass from the expandable balloon portion 24 to the fluid reservoir portion 22. Although further confirmation that such idiosyncratic narrowings of the urinary passageway 68 of certain patients will cause this problem is still being sought, the present Applicants envision several alternate embodiments of the present hand-actuated retention catheter 5 which will enable the Applicants to address this problem should it arise. It will be appreciated that the Applicants have not as yet tested any of these envisioned solutions, and that the preferred embodiment which is ultimately selected, has as yet to be fully designed, developed, tested and manufactured. It will be appreciated, however, that embodiments of the present hand-actuated retention catheter 5 which have additional features to address this problem include, but are not limited to, the following alternate embodiments of the catheter.

Referring now also to FIGS. 22–24, an alternate hand-actuated retention catheter 5' is disclosed which is almost identical to the hand-actuated retention catheter 5 shown in FIGS. 1–9, and will operate in virtually the same manner. The alternate embodiment, however, will have one significant difference. When making the alternate catheter 5', the alternate intermediate tube 12' will include a pair of grooves 13,15 in the outer surface 20'. In the finished alternate catheter 5', these grooves 13,15 will extend only from a point within the catheter sleeve portion 26' distal to the location of the resilient disc 50', to a point within the expandable balloon portion 24' of the cavity 16'. In this way, the resilient disc 50' will function just as its counterpart disc 50, functioned in the preferred catheter 5. In the alternate catheter 5', if the urinary passageway 68 narrows so as to force the catheter sleeve section 34' of the overcoat layer 14' down upon the circumference of the outer surface 20' of the tube 12', fluid 18' will still be able to flow from the expandable balloon portion 24' through the grooves 13,15 within the otherwise closed-off catheter sleeve portion 26'. The fluid 18 will flow into the fluid reservoir portion 22' under the force of the resilient expandable balloon section 32' when the expandable balloon section 32' is in an expanded position and the resilient disc 50' is deformed in a manner similar to that shown for the preferred catheter 5 in FIG. 7. In preferred embodiments of the alternate catheter 5', the alternate intermediate tube (not shown) used to make the tube 12' is preferably injection-molded, preferably of a suitable silicone rubber material.

Figure 27:
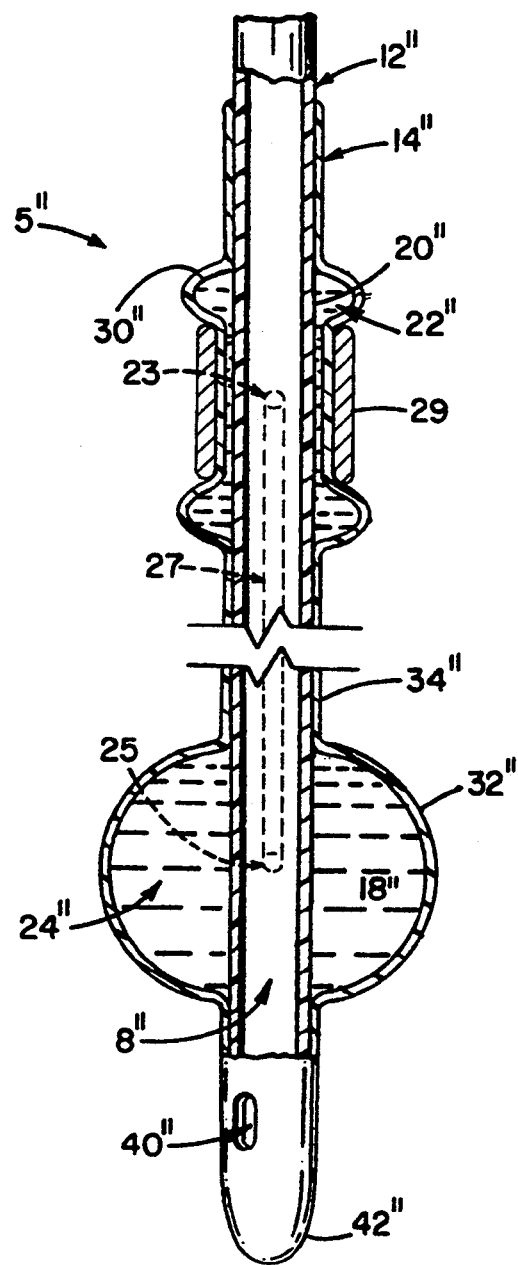
FIG. 27 is a transverse schematic view of a portion of the alternate retention catheter shown in FIG. 25, showing the balloon section in an expanded state and the fluid reservoir section in a compressed state.

In yet other alternate embodiments (not shown), grooves (not shown) similar to grooves 13,15 of the alternate catheter 5' shown in FIGS. 22–24, may extend all the way from the corresponding expandable balloon portion (not shown) to the corresponding fluid reservoir portion (not shown). In such an embodiment, the corresponding alternate tube (not shown) could also be injection molded. If the grooves (not shown) are designed to extend the entire length of yet another corresponding alternate tube (not shown), the corresponding alternate tube (not shown) could also be an extruded tube to which a molded tip is subsequently attached. In these two latter embodiments, neither of the corresponding alternate catheters (not shown) will need to have a resilient restriction disc corresponding to that shown in FIGS. 1–9. In such a case, some type of resilient band (not shown), a clamping mechanism (not shown), or any other effective mechanism for compressing and retaining the corresponding fluid reservoir section (not shown) in a compressed state, generally similar to that shown for the preferred catheter 5 in FIGS. 5 and 9, will be necessary to prevent the respective corresponding expandable balloon sections (not shown) from deflating once they have been expanded (such a device is shown in FIG. 27 for yet another embodiment). Since the groove or grooves (not shown) in the outer surface of the corresponding alternate tubes will extend all the way from the corresponding alternate expandable balloon portion (not shown) to the corresponding alternate fluid reservoir portion (not shown) of the corresponding alternate cavities (not shown), the fluid will be able to pass from one to the other even when the corresponding alternate catheter sleeve section (not shown) is pressed against the circumference of the corresponding alternate outer surfaces of the corresponding alternate tubes in these respective embodiments.

Alternately, the grooves 13,15 shown in FIG. 24 is envisioned where a further embodiment (not shown) similar to the alternate catheter 5', including grooves similar to the corresponding overcoat layer (not shown) is secured directly to the outer surface (not shown) of the tube (not shown), except where the outer surface recesses within the respective grooves.

Referring now also to FIGS. 25–29, yet further embodiments of the present invention could provide a corresponding alternate tube 5" which has a plurality of lumens 8", 27, one of which (27) communicates only with a first cavity 22", corresponding with the fluid reservoir portion 22 of the preferred catheter 5, and a second cavity 24", corresponding to the expandable balloon portion 24 of the preferred catheter 5, via access openings 23 and 25, respectively. In this alternate embodiment, there is no corresponding third cavity interconnecting the first and second cavities and corresponding to the catheter sleeve portion 26 of the preferred catheter 5. In this alternate embodiment, however, it is again necessary to have a mechanism, such as the releasable band mechanism 29 shown in FIG. 27, for compressing the first cavity and holding it in a compressed state such that the second cavity remains in an expanded state so as to provide a suitable retention mechanism for retaining this alternate catheter 5" within a urinary passageway (not shown). It will be appreciated that the second lumen 27 of the alternate catheter 5" will allow fluid 18" to communicate at will between the respective first and second cavities 22",24", whether or not there is a corresponding third cavity interconnecting and communicating with each of the respective first and second cavities.

In yet further alternate embodiments of the present catheter 5 which are similar to the latter alternate embodiment 5", a second lumen (not shown) may communicate between any of the respective first, second and third corresponding alternate cavities. In a specific alternate embodiment envisioned by the Applicants, a second lumen 27 passing through the alternate tube 12" will interconnect first and second alternate cavities 22" and 24", corresponding to the fluid reservoir portion 22 and the expandable balloon portion 24, respectively, of the preferred catheter 5, and there will be no other means of communication between the respective alternate cavities. In a further variation 5''' of this alternate catheter 5", shown in FIGS. 28 and 29, the first reservoir 22''' will include a cylindrical narrowing distal thereto and extending toward, but not communicating with, the second cavity 24'''. The access opening 23''' for the second lumen 27''' communicates with the first cavity 22''' within this narrowing, such that an alternate resilient disc 50''' similar to the disc 50 shown in FIG. 1 can be used to restrict the flow of fluid 18''' from the narrowed extension portion of the first cavity 22''' into a larger portion thereof having greater capacity to contain the fluid 18'''. In this way, this alternate retention catheter 5''' can be provided with a resilient retention disc 50''' which can be used in a similar way to the retention disc 50 shown in FIG. 1. However, a narrowing of the urinary passageway 68 proximate the neck of the bladder which compresses the overcoat layer 14''' of the alternate catheter 5''' will not prevent fluid communication between the respective corresponding first and second cavities 22''' and 24'''.

It is to be understood, however, that even though numerous characteristics and advantages of the present invention have been set forth in the foregoing description, together with details of the structure and function of the invention, the sequence or order of the specific steps, or the actual compositions, solvents, temperatures, environmental conditions and the like employed for each step, it will be appreciated the disclosure is illustrative only, and that changes may be made in detail, especially in matters of shape, size, arrangement of parts or sequence or elements of events within the principles of the invention to the full extent indicated by the broad general meaning of the terms in which the appended claims are expressed.

What is claimed is:

1. A hand-actuated retention catheter, comprising;
a tube having outer and inner surfaces, the inner surface defining an inner lumen, an overcoat layer encircling the tube, the overcoat layer having interior and exterior surfaces, a cavity interposed between the tube and the overcoat layer, said cavity encircling the tube and being defined by portions of the outer surface of the tube in cooperation with portions of the interior surface of the overcoat layer, and a fluid within the cavity; wherein the overcoat layer includes an expandable balloon section, a fluid reservoir section, and a catheter sleeve section interconnecting said reservoir section and said sleeve section; the overcoat layer being joined to the outer surface of the tube at distal and proximal ends of the cavity; the cavity including an expandable balloon portion, a fluid reservoir portion, and a catheter sleeve portion interconnecting the reservoir portion and the sleeve portion; restriction means disposed on the sleeve section for restricting the passage of fluid between the expandable balloon portion and the fluid reservoir portion via the catheter sleeve portion of the cavity, wherein the restriction by said restriction means does not substantially lower the volume of the fluid reservoir portion; wherein the catheter sleeve section of the overcoat layer defines a narrowing in the cavity through which fluid passing from the fluid reservoir portion to the expandable balloon portion thereof must pass.

2. The hand-actuated retention catheter of claim 1 wherein said restriction means include a resilient restriction disc having an inner perimeter defining an opening through which the catheter sleeve section of the overcoat layer passes, wherein the inner perimeter presses the catheter sleeve section against the outer surface of the tube along an entire circumference thereof so as to prevent fluid from passing through the catheter sleeve portion of the cavity when the reservoir is not compressed.

3. The hand-actuated retention catheter of the claim 1 wherein the catheter sleeve portion of the cavity is at least about 0.5 inches long.

4. The hand-actuated retention catheter of claim 1 wherein the expandable balloon portion of the cavity can be expanded solely by grasping the fluid retention section of the overcoat layer and compressing the fluid retention portion of the cavity.

5. The hand-actuated retention catheter of claim 4 wherein the expandable balloon section of the overcoat layer is a resilient material which, when expanded to a fully expanded state, will return to a normal, unexpanded state when fluid is allowed to pass out of the expandable balloon portion of the cavity.

6. The hand-actuated retention catheter of claim 5 wherein said restriction means include an expandable restriction disc having an expandable inner perimeter encircling and pressing the catheter sleeve section of the overcoat layer such that fluid passing between the expandable balloon portion and the fluid reservoir portion of the cavity via the catheter sleeve portion thereof is restricted by the expandable restriction disc when the reservoir is not compressed; and wherein fluid can pass between the expandable balloon portion and the fluid retention portion of the cavity via the catheter sleeve portion thereof when the expandable inner perimeter of the restriction disc is expanded such that fluid can pass between the catheter sleeve section of the overcoat layer and the outer surface of the tube encircled by the expandable restriction disc.

7. The hand-actuated retention catheter of claim 6 wherein the expandable perimeter of the restriction disc is expandable by fluid pressure to allow fluid to pass through the catheter sleeve portion by hand compression of the reservoir portion of the cavity.

8. The hand-actuated retention catheter of claim 1 wherein the overcoat layer has a uniform thickness and includes an expandable balloon section, a fluid reservoir section, and a catheter sleeve section.

9. A hand-actuated catheter, comprising:
a silicone rubber tube having outer and inner surfaces, the inner surface defining an inner lumen, silicone rubber-containing overcoat layer encircling the tube, the overcoat layer having interior and exterior surfaces, a cavity interposed between the tube and the overcoat layer, said cavity encircling the tube and being defined by portions of the outer surface of the tube in cooperation with portions of the interior surface of the overcoat layer, and a fluid within the cavity; wherein the overcoat layer includes an expandable balloon section, a fluid reservoir section, and a catheter sleeve section interconnecting said reservoir section and said sleeve section; the overcoat layer being joined to the outer surface of the tube at distal and proximal ends of the cavity; the cavity including an expandable balloon portion, a fluid reservoir portion, and a catheter sleeve portion interconnecting the reservoir portion and the sleeve portion; wherein the catheter sleeve section of the overcoat layer defines a narrowing in the cavity through which fluid passing from the fluid reservoir portion to the expandable balloon portion thereof must pass;
the hand-actuated retention catheter being made by a process comprising the steps of:
(a) providing a silicone rubber tube;
(b) initially coating portions of an outer surface of such silicone rubber tube with a bond preventing agent in a plurality of dipping steps, wherein the tube is immersed into the bond preventing agent to a desired depth for a desired length of time, and subsequently removed, said plurality of dipping steps being automated in series by mechanized automation means including computer control means, wherein the desired depth and the length of time for each of the plurality of dipping steps is prescribed so that a residual coating of bond preventing agent remains on portions of the silicone rubber tube following said plurality of dipping steps, said residual coating having a variable thickness as a result of a variation between the depth of any two of said plurality of dipping steps; and
(c) subsequently coating the silicone rubber tube and the residual coating of bond preventing agent with a polymeric bonding composition containing silicone rubber to form a shaped overcoat layer, wherein the shape of the overcoat layer results in part from the variable thickness of the residual coating.

10. The hand-actuated retention catheter of claim 9 wherein the overcoat layer of the catheter is shaped to include a bulbous balloon section interconnected to a cylindrical sleeve section.

11. The hand-actuated retention catheter of claim 10 wherein the overcoat layer is shaped to include an enlarged cylindrical fluid reservoir section interconnected with and separated from the bulbous balloon section by the cylindrical sleeve section.

12. A method of using a hand-actuated retention catheter, said method comprising the steps of:
 (a) providing a hand-actuated retention catheter including a tube having outer and inner surfaces, the inner surface defining an inner lumen, an overcoat layer encircling the tube, the overcoat layer having interior and exterior surfaces, a cavity interposed between the tube and the overcoat layer, said cavity encircling the tube and being defined by portions of the outer surface of the tube in cooperation with portions of the interior surface of the overcoat layer, and a fluid within the cavity; wherein the overcoat layer includes an expandable balloon section, a fluid reservoir section, and a catheter sleeve section interconnecting said reservoir section and said sleeve section; the overcoat layer being joined to the outer surface of the tube at distal and proximal ends of the cavity; the cavity including an expandable balloon portion, a fluid reservoir portion, and a catheter sleeve portion interconnecting the reservoir portion and the sleeve portion; restriction means disposed on the sleeve section for restricting the passage of fluid between the expandable balloon portion and the fluid reservoir portion via the catheter sleeve portion of the cavity; wherein the catheter sleeve section of the overcoat layer defines a narrowing in the cavity through which fluid passing from the fluid reservoir portion to the expandable balloon portion thereof must pass;
 (b) inserting the hand-actuated retention catheter into a urinary passageway of a person; and
 (c) compressing the fluid reservoir section, thereby forcing fluid out of the fluid reservoir portion of the cavity and into the expandable balloon portion thereof so as to expand the expandable balloon section of the overcoat layer, wherein the retention catheter is retained within the urinary passageway.

13. The method of claim 12 wherein said restriction means include a resilient restriction disc having an inner perimeter defining an opening through which the catheter sleeve section of the overcoat layer passes, wherein the inner perimeter presses the catheter sleeve section against the outer surface of the tube along an entire circumference thereof so as to prevent fluid from passing through the catheter sleeve portion of the cavity when the reservoir is not compressed but allows fluid to pass through when the reservoir is compressed; and further comprising deflating the expandable balloon section by pulling opposite sides of said resilient retention disc in opposite directions to permit fluid to pass through the catheter sleeve portion of the cavity.

14. A hand-actuated retention catheter, comprising: a tube having an inner lumen and an outer surface, an expandable retention balloon including a balloon cavity external to said inner lumen, a fluid reservoir including a fluid reservoir cavity external to said inner lumen, fluid communication means for permitting fluid communication between said fluid reservoir cavity and said balloon cavity, and an amount of fluid in the fluid reservoir cavity and the balloon cavity sufficient to expand the expandable balloon when the fluid reservoir is compressed, said balloon, fluid reservoir, and fluid communication means have a common overcoat layer attached to said tube at at least one point proximal of said fluid reservoir cavity; wherein the fluid reservoir can be compressed so as force fluid from the fluid reservoir cavity into the balloon cavity via said fluid communication means such that the expandable retention balloon expands.

15. The hand-actuated retention catheter of claim 14 wherein said fluid communication means include a cylindrical cavity encircling said tube and interconnecting the fluid reservoir cavity with the balloon cavity.

16. The hand-actuated retention catheter of claim 15 wherein said retention catheter further comprises restriction means for restricting the passage of fluid between the fluid reservoir cavity and the balloon cavity.

17. The hand-actuated retention catheter of claim 16 wherein said restriction means include a resilient restriction disc encircling said retention catheter proximate said cylindrical cavity.

18. The hand-actuated retention catheter of claim 14 wherein said fluid communication means include a groove on the outer surface of said tube.

19. The hand-actuated retention catheter of claim 14 wherein said fluid communication means include a second lumen in said tube which communicates with said fluid reservoir cavity and said balloon cavity.

20. A hand-actuated retention catheter, comprising: a tube having an inner lumen and an outer surface, an expandable retention balloon including a balloon cavity external to said inner lumen, a fluid reservoir including a fluid reservoir cavity external to said inner lumen, fluid communication means for permitting fluid communication between said fluid reservoir cavity and said balloon cavity, and an amount of fluid in the fluid reservoir cavity and the balloon cavity sufficient to expand the expandable balloon when the fluid reservoir is compressed, said balloon has an overcoat layer that extends to cover a distal tip of said catheter; wherein the fluid reservoir can be compressed so as to force fluid from the fluid reservoir cavity into the balloon cavity via said fluid communication means such that the expandable retention balloon expands.

* * * * *